United States Patent
Kapeller-Libermann et al.

(10) Patent No.: US 6,673,564 B2
(45) Date of Patent: *Jan. 6, 2004

(54) METHODS FOR USING 22045, A HUMAN CYCLIC NUCLEOTIDE PHOSPHODIESTERASE

(75) Inventors: Rosana Kapeller-Libermann, Chestnut Hill, MA (US); John Joseph Hunter, Somerville, MA (US); Mark Williamson, Saugus, MA (US)

(73) Assignee: Millennium Pharmaceuticals, Inc., Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/420,190

(22) Filed: Oct. 18, 1999

(65) Prior Publication Data

US 2002/0081633 A1 Jun. 27, 2002

(51) Int. Cl.[7] .................................. C12Q 1/44
(52) U.S. Cl. .......................... 435/19; 435/196
(58) Field of Search ................... 435/7.21, 19, 196

(56) References Cited

U.S. PATENT DOCUMENTS

| | | | | |
|---|---|---|---|---|
| 5,798,246 A | * | 8/1998 | Au-Young et al. | 435/196 |
| 5,932,465 A | * | 8/1999 | Loughney | 435/196 |
| 6,100,037 A | * | 8/2000 | Phillips et al. | 435/6 |
| 6,114,111 A | * | 9/2000 | Luo et al. | 435/5 |

FOREIGN PATENT DOCUMENTS

| EP | 0 967 284 A1 | 12/1999 |
|---|---|---|
| WO | WO 99/19495 A1 | 4/1999 |

OTHER PUBLICATIONS

Ealey et al. (1987) J Endocrinol 114:199–205.*
Fugishige et al. (1999) "Cloning and Characterization of a Novel Human Phosphodiesterase that Hydrolyzes Both cAMP and cGMP (PDE10A)," *The Journal of Biological Chemistry 274*: 18438–18445.
Kotera et al. (1999) "Characterization and Phosphorylation of PDE10A2, A Novel Alternative Splice Variant of Human Phosphodiesterase that Hydrolyzes cAMP and cGMP," *Biochemical and Biophysical Research Communications 261*: 551–557.
Loughney et al. (1999) "Isolation and Characterization of PDE10A, A Novel Human 3', 5'–Cyclic Nucleotide Phosphodiesterase," *Gene 234*: 109–117.
Scott et al., "Searching for Peptide Ligands with an Epitope Library," *Science* (Jul. 27, 1990), pp. 386–390, vol. 249.

* cited by examiner

*Primary Examiner*—Rebecca E. Prouty
*Assistant Examiner*—David J. Steadman
(74) *Attorney, Agent, or Firm*—Millennium Pharmaceuticals, Inc.

(57) ABSTRACT

The present invention relates to methods for using a human cyclic nucleotide phosphodiesterase belonging to the superfamily of mammalian phosphodiesterases. The invention also relates to methods for using polynucleotides encoding the phosphodiesterase. The invention relates to methods using the phosphodiesterase polypeptides and polynucleotides as a target for diagnosis and treatment in phosphodiesterase-mediated or -related disorders. The invention further relates to drug-screening methods using the phosphodiesterase polypeptides and polynucleotides to identify agonists and antagonists for diagnosis and treatment. The invention further encompasses agonists and antagonists based on the phosphodiesterase polypeptides and polynucleotides. The invention further relates to agonists and antagonists identifiefd by drug screening methods with the phosphodiesterase polypeptides and polynucleotides as a target.

12 Claims, 12 Drawing Sheets

```
Input file Fbh22045.seq;  Output File 22045.trans
Sequence length 4381
         10        20        30        40        50        60       M   R   I     3
CATCCACAGAGATGTTACAGTTGAAGAGATGGGGGTAGAGAAGACTTTGAAGGAAAAGAATGTAGA ATG AGG ATA     9    75
  E   E   R   K   S   Q   H   L   T   G   L   T   D   E   K   V   K   A   Y   L    23
GAA GAG AGG AAA TCC CAA CAT TTA ACA GGT TTG ACA GAT GAA AAA GTG AAG GCA TAT CTT    69   135
  S   L   H   P   Q   V   L   D   E   F   V   S   E   S   V   S   A   E   T   V    43
TCT CTT CAC CCC CAG GTA TTA GAT GAA TTT GTA TCT GAA AGT GTT AGT GCA GAG ACA GTA   129   195
  E   K   W   L   K   R   K   N   N   K   S   E   D   E   S   A   P   K   E   V    63
GAG AAA TGG CTG AAG AGG AAG AAC AAC AAA TCA GAA GAT GAA TCG GCT CCT AAG GAA GTC   189   255
  S   R   Y   Q   D   T   N   M   Q   G   V   V   Y   E   L   N   S   Y   I   E    83
AGC AGG TAC CAA GAT ACG AAT ATG CAG GGA GTT GTA TAT GAA CTA AAC AGC TAT ATA GAA   249   315
  Q   R   L   D   T   G   G   D   N   Q   L   L   L   Y   E   L   S   S   I   I   103
CAA CGG TTG GAC ACA GGA GGA GAC AAC CAG CTA CTC CTC TAT GAA CTG AGC AGC ATC ATT   309   375
  K   I   A   T   K   A   D   G   F   A   L   Y   F   L   G   E   C   N   N   S   123
AAA ATA GCC ACA AAA GCC GAT GGA TTT GCA CTG TAT TTC CTT GGA GAG TGC AAT AAT AGC   369   435
  L   C   I   F   T   P   P   G   I   K   E   G   K   P   R   L   I   P   A   G   143
CTG TGT ATA TTC ACG CCA CCT GGG ATA AAG GAA GGA AAA CCC CGC CTC ATC CCT GCT GGG   429   495
  P   I   T   Q   G   T   T   V   S   A   Y   V   A   K   S   R   K   T   L   L   163
CCC ATC ACT CAG GGC ACC ACC GTC TCT GCT TAT GTG GCC AAG TCC AGG AAA ACA CTG CTA   489   555
  V   E   D   I   L   G   D   E   R   F   P   R   G   T   G   L   E   S   G   T   183
GTA GAA GAC ATC CTT GGA GAT GAA CGA TTT CCA AGA GGT ACT GGA CTG GAA TCA GGG ACT   549   615
  R   I   Q   S   V   L   C   L   P   I   V   T   A   I   G   D   L   I   G   I   203
CGT ATC CAG TCT GTT CTT TGC TTA CCA ATT GTC ACT GCA ATT GGT GAC TTG ATT GGT ATT   609   675
  L   E   L   Y   R   H   W   G   K   E   A   F   C   L   S   H   Q   E   V   A   223
CTC GAG CTG TAT CGG CAC TGG GGC AAA GAA GCC TTC TGT CTT AGT CAC CAG GAG GTT GCA   669   735
  T   A   N   L   A   W   A   S   V   A   I   H   Q   V   Q   V   C   R   G   L   243
ACA GCA AAT CTT GCC TGG GCT TCA GTA GCA ATA CAT CAG GTG CAG GTA TGC AGA GGC CTT   729   795
  A   K   Q   T   E   L   N   D   F   L   L   D   V   S   K   T   Y   F   D   N   263
GCC AAA CAG ACA GAA TTG AAT GAC TTC CTA CTC GAC GTA TCA AAA ACA TAT TTT GAT AAC   789   855
  I   V   A   I   D   S   L   L   E   H   I   M   I   Y   A   K   N   L   V   N   283
ATA GTT GCA ATA GAT TCT CTA CTT GAA CAC ATA ATG ATA TAT GCA AAA AAC CTG GTG AAT   849   915
  A   D   R   C   A   L   F   Q   V   D   H   K   N   K   N   K   E   L   Y   S   D   L   303
GCC GAT CGT TGT GCA CTT TTC CAG GTG GAC CAT AAG AAC AAG GAG TTA TAT TCA GAC CTT   909   975
  F   D   I   G   E   E   K   E   G   K   P   V   F   K   K   T   K   E   I   R   323
TTT GAT ATT GGA GAG GAA AAG GAA GGA AAA CCT GTC TTC AAG AAG ACC AAA GAG ATA AGA   969  1035
  F   S   I   E   K   G   I   A   G   Q   V   A   R   T   G   E   V   L   N   I   343
TTT TCA ATT GAG AAA GGA ATT GCT GGC CAA GTA GCA AGA ACA GGG GAA GTC CTG AAC ATT  1029  1095
  P   D   A   Y   A   D   P   R   F   N   R   E   V   D   L   Y   T   G   Y   T   363
CCA GAT GCC TAT GCA GAC CCA CGC TTT AAC AGA GAA GTA GAC TTG TAC ACA GGC TAC ACC  1089  1155
  T   R   N   I   L   C   M   P   I   V   S   R   G   S   V   I   G   V   V   Q   383
```

FIG. 1A.

```
                                                                              1149 1215
ACG CGG AAC ATC CTG TGC ATG CCC ATC GTC AGC CGA GGC AGC GTG ATA GGT GTG GTG CAG
 M   V   N   K   I   S   G   S   A   F   S   K   T   D   E   N   N   F   K   M    403
ATG GTC AAC AAA ATC AGT GGC AGT GCC TTC TCT AAA ACA GAT GAA AAC AAC TTC AAA ATG 1209 1275
 F   A   V   F   C   A   L   A   L   H   C   A   N   M   Y   H   R   I   R   H    423
TTT GCC GTC TTT TGT GCT TTA GCC TTA CAC TGT GCT AAT ATG TAT CAT AGA ATT CGC CAC 1269 1335
 S   E   C   I   Y   R   V   T   M   E   K   L   S   Y   H   S   I   C   T   S    443
TCA GAG TGC ATT TAC CGG GTA ACG ATG GAA AAG CTG TCC TAC CAT AGC ATT TGT ACT TCA 1329 1395
 E   E   W   Q   G   L   M   Q   F   T   L   P   V   R   L   C   K   E   I   E    463
GAA GAG TGG CAA GGT CTC ATG CAA TTC ACC CTT CCC GTG CGT CTC TGC AAA GAA ATT GAA 1389 1455
 L   F   H   F   D   I   G   P   F   E   N   M   W   P   G   I   F   V   Y   M    483
TTA TTC CAC TTT GAC ATT GGT CCT TTT GAA AAC ATG TGG CCT GGA ATT TTT GTC TAC ATG 1449 1515
 V   H   R   S   C   G   T   S   C   F   E   L   E   K   L   C   R   F   I   M    503
GTT CAT CGG TCC TGT GGG ACA TCC TGC TTT GAG CTT GAA AAG TTG TGT CGT TTT ATT ATG 1509 1575
 S   V   K   K   N   Y   R   R   V   P   Y   H   N   W   K   H   A   V   T   V    523
TCT GTG AAG AAG AAC TAT CGG CGG GTT CCT TAT CAC AAC TGG AAG CAT GCG GTC ACT GTA 1569 1635
 A   H   C   M   Y   A   I   L   Q   N   N   H   T   L   F   T   D   L   E   R    543
GCA CAC TGC ATG TAT GCC ATA CTT CAG AAC AAT CAC ACG CTT TTC ACA GAC CTT GAG CGC 1629 1695
 K   G   L   L   I   A   C   L   C   H   D   L   D   H   R   G   F   S   N   S    563
AAA GGA CTG CTG ATT GCG TGT CTG TGT CAT GAC CTG GAC CAC AGG GGC TTC AGT AAC AGC 1689 1755
 Y   L   Q   K   F   D   H   P   L   A   A   L   Y   S   T   S   T   M   E   Q    583
TAC CTG CAG AAG TTC GAC CAC CCT CTG GCC GCT CTC TAC TCC ACT TCC ACC ATG GAG CAG 1749 1815
 H   H   F   S   Q   T   V   S   I   L   Q   L   E   G   H   N   I   F   S   T    603
CAC CAC TTC TCC CAG ACT GTG TCC ATC CTC CAG TTG GAA GGG CAC AAT ATC TTC TCC ACT 1809 1875
 L   S   S   S   E   Y   E   Q   V   L   E   I   I   R   K   A   I   I   A   T    623
CTG AGC TCC AGT GAA TAT GAG CAG GTG CTT GAG ATC ATC CGC AAA GCC ATC ATT GCC ACA 1869 1935
 D   L   A   L   Y   F   G   N   R   K   Q   L   E   E   M   Y   Q   T   G   S    643
GAC CTT GCT TTA TAC TTT GGA AAC AGG AAG CAG TTG GAA GAG ATG TAC CAG ACC GGA TCA 1929 1995
 L   N   L   N   N   Q   S   H   R   D   R   V   I   G   L   M   M   T   A   C    663
CTA AAC CTT AAT AAT CAA TCA CAT AGA GAC CGT GTA ATT GGT TTG ATG ATG ACT GCC TGT 1989 2055
 D   L   C   S   V   T   K   L   W   P   V   T   K   L   T   A   N   D   I   Y    683
GAC CTT TGT TCT GTG ACA AAA CTG TGG CCC GTT ACA AAA TTG ACG GCA AAT GAT ATA TAT 2049 2115
 A   E   F   W   A   E   G   D   E   M   K   K   L   G   I   Q   P   I   P   M    703
GCA GAA TTC TGG GCT GAG GGT GAT GAA ATG AAG AAA TTG GGA ATA CAG CCT ATT CCT ATG 2109 2175
 M   D   R   D   K   K   D   E   V   P   Q   G   Q   L   G   F   Y   N   A   V    723
ATG GAC AGA GAC AAG AAG GAT GAA GTC CCC CAA GGC CAG CTT GGG TTC TAC AAT GCC GTG 2169 2235
 A   I   P   C   Y   T   T   L   T   Q   I   L   P   P   T   E   P   L   L   K    743
GCC ATT CCC TGC TAT ACA ACC CTT ACC CAG ATC CTC CCT CCC ACG GAG CCT CTT CTG AAA 2229 2295
 A   C   R   D   N   L   S   Q   W   E   K   V   I   R   G   E   E   T   A   T    763
GCA TGC AGG GAT AAT CTC AGT CAG TGG GAG AAG GTG ATT CGA GGG GAG GAG ACT GCA ACC 2289 2355
 W   I   S   S   P   S   V   A   Q   K   A   A   S   E   D   *                    780
TGG ATT TCA TCC CCA TCC GTG GCT CAG AAG GCA GCT GCA TCT GAA GAT TGA              2340
                                                                      2403
```

FIG. 1B.

```
GCACTGGTCACCCTGACACGCTGTCCCACCTACAGATCCTCATCTTGCTTCTTTGACATTCTTTTCCTTTTTTTGGGGG
GGGTGGGGGGAACCTGCACCTGGTAACTGGGGTGCAAACCTCTTCAAGAAGGTAACATCAAATAAATAAGTCAAGCAGA
GGACTTCCTGCCAATCTCTTCTGTGAGGCATCATAGACACTGAGCAACCAGGACCACCCCACGTTCAGAAATCAGCTG
GCCAAGTGACTCCATTTGACTTGCAAACCAGCCTTTTCTAATAGGCTAATATTGCTGAGGCCTTAAAGGAAATGGACAA
AAATTATCCAGAAGGGGTACTTTTCCATTGTATCTTTCTAATAAGGGTTTAAAATGGTACTATTATGGTATTGTACTTG
GGCTTTAACATCAATGTTGCTTTGATGTTGTTGGATATAAATAGGAATTTTTACACATTACTATTGTGAATGGTGAATG
TTCATGTATGACCTACTTGTAATTAACTTGAGTTGTAGTCCACAGCCTCAGGACAAATGTCGTTGAGGTTACAGAGTAA
GAAATGATGGCAAAACGTCAAACTCTTATTTCAGAGCTTCATGAATTTAGTTAGACTAAACATAATTCTTTAAGTTCAA
CCTAAAGGGCTGAGATCAATAAATTTAACACTAGACGAAGTAGACTTCCTGTCTTTTTGAGAAGAGATGAGGTATATGT
TACAATAAATCTCAGAACTTCAAGTAGCAGTTCAAAAGATGTCAGTTTTTAAAATTGTTTTTTGTGTTGTCTTGGCAGT
TTTACTGAACCCTTTGCATAAAGAACAAAATAAAAGCTCGGCATTGTAATTTTTTTAATGGACAAGTCTTATGGATACG
AAGGGTACATTTTTCATAATGATTCCTTTATATTTTCACTTTGTGTCATTGCAGAATTTTAGACTCTCATTCACAATGA
AAAGTTTATTTTAAACATTGTTTAATTAAAATACCATACAGTTCTCTTTTAAACATCAAACCATAAAAAGTGATTTTG
TAATTTTACTCTGACCTGCCGCAGTCACCTCTCACTTATCTCTTCCACGTACTGCACGGTCGTATTTCATGAGCTTTCT
GTCCATAGCACAGAAACAGAGCAGAAAGTAGTACAATCATGTTGGACCTTCTTTCTGTTCTCTTTACTCTTCTCACAGA
TCAGATCACTCCATAGAAGCCTGTGGGTTTCGATGGTTTCTTCTATACACCTTTTTGGTTGACCAGTATTACTATACAA
TGTAAGTGTTTAAAAAAATACGAAAGTAATACTCTGCACCCCTTCCTACAAAGATGATAAAGCAGTCACTTCTGGCGCA
TTTTAATAATTTAAAGATTTTTAGTGCAATGGCACGGTAACCTCCAAACCTGAATTAGACAGAGACTCACTCAGGAAGT
GACAGGCCCATCATATCAAATAACTTATTCACTTTTCATGTGGCAGGAAACTGGAATATCGCTTTTAATAAAATGGAAA
AATATGCTTCTACATATTTACCACCATAGGCGTTTTGTTCATATGAGCCTGGTTTGTGCAAAATTAAATCAGAGGCTTC
TACAACATGGTTTATTTATGTTGTAGCAAAGTTGGCTCTACATAAACATTGTTCTTATTTTAAAATTAACACTATGTGT
TCAGTTTTCTTGTGGGCTTCTGAAAGTTGCCATCTTCCCTCCGTGGAGCTCCATTTGCTATTTTCATTATACACTATGA
GGTAAAATGTAATAACAAAAGAGAGAGAAGTACCACTGTGGCTAGATATATACACACACATATATATATGGATGGATGT
AATATATGTAGAACACACACATAGATGTATATAGGATACACACTCATGTATGTAAACGTATACATATGTGTATATATGA
TACATACACATACACACACACGAGAGACAGAAGGAAAGAGAGGAAGAGAGAAGCAAACATGTAGGAAAAAATATAAATC
TACATACACATACACACACACGAGAGACAGAAGGAAAGAGAGGAAGAGAGAAGCAAACATGTAGGAAAAAATATAAATC
```

FIG. 1C.

Transmembrane Segments Predicted by MEMSAT

| Start | End | Orient | Score |
|-------|-----|--------|-------|
| 187 | 204 | out-->ins | 2.5 |
| 403 | 419 | ins-->out | 2.3 |
| 655 | 672 | out-->ins | 0.5 |

FIG. 4A.

Prosite Pattern Matches for 22045

>PS00001/PDOC00001/ASN_GLYCOSYLATION N-glycosylation site.

Query: 52    NKSE    55
Query: 121   NNSL    124
Query: 534   NHTL    537
Query: 648   NQSH    651
Query: 748   NLSQ    751

>PS00005/PDOC00005/PKC_PHOSPHO_SITE Protein kinase C phosphorylation site.

Query: 158   SRK    160
Query: 363   TTR    365
Query: 504   SVK    506
Query: 650   SHR    652

>PS00006/PDOC00006/CK2_PHOSPHO_SITE Casein kinase II phosphorylation site.

Query: 54    SEDE    57
Query: 80    SYIE    83
Query: 88    TGGD    91
Query: 107   TKAD    110
Query: 177   TGLE    180
Query: 218   SHQE    221
Query: 259   TYFD    262
Query: 269   SLLE    272
Query: 394   SKTD    397
Query: 442   TSEE    445
Query: 491   SCFE    494
Query: 539   TDLE    542
Query: 579   STME    582
Query: 605   SSSE    608
Query: 650   SHRD    653
Query: 661   TACD    664
Query: 678   TAND    681
Query: 750   SQWE    753

>PS00007/PDOC00007/TYR_PHOSPHO_SITE Tyrosine kinase phosphorylation site.

Query: 351   RFNREVDLY    359
Query: 422   RHSECITY     428
Query: 429   RVTMEKLSY    437
Query: 632   RKQLEEMY     639

>PS00008/PDOC00008/MYRISTYL N-myristoylation site.

Query: 131   GIKEGK    136
Query: 148   GTTVSA    153

FIG. 4B.

| Query: | 178 | GLESGT | 183 |
| Query: | 376 | GSVIGV | 381 |
| Query: | 390 | GSAFSK | 395 |
| Query: | 545 | GLLIAC | 550 |
| Query: | 657 | GLMMTA | 662 |

FIG. 4C.

>PS00126/PDOC00116/PDEASE_I 3'5'-cyclic nucleotide phosphodiesterases signature.

Query: 553   HDLDHRGFSNSY   564

METHODS FOR USING 22045, A HUMAN CYCLIC NUCLEOTIDE PHOSPHODIESTERASE

FIELD OF THE INVENTION

The present invention relates to methods for using a human cyclic nucleotide phosphodiesterase. The invention also relates to methods for using polynucleotides encoding the phosphodiesterase. The invention further relates to methods using the phosphodiesterase polypeptides and polynucleotides as a target for diagnosis and treatment in phosphodiesterase-mediated or -related disorders. The invention further relates to drug-screening methods using the phosphodiesterase polypeptides and polynucleotides to identify agonists and antagonists for diagnosis and treatment. The invention further encompasses agonists and antagonists based on the phosphodiesterase polypeptides and polynucleotides. The invention further relates to agonists and antagonists identified by drug screening methods with the phosphodiesterase polypeptides and polynucleotides as a target.

BACKGROUND OF THE INVENTION

Cyclic nucleotide phosphodiesterases show specificity for purine cyclic nucleotide substrates and catalyze cyclic AMP (cAMP) and cyclic GMP (cGMP) hydrolysis (Thompson W. J. (1991) *Pharma. Ther.* 51:13–33). Cyclic nucleotide phosphodiesterases regulate the steady-state levels of cAMP and cGMP and modulate both the amplitude and duration of cyclic nucleotide signal. At least eight different but homologous gene families are currently known to exist in mammalian tissues. Most families contain distinct genes, many of which are expressed in different tissues as functionally unique alternative splice variants (Beavo (1995) *Physiological Reviews* 75:725–748 and U.S. Pat. No. 5,798,246).

All cyclic nucleotide phosphodiesterases contain a core of about 270 conserved amino acids in the COOH-terminal half of the protein thought to be the catalytic domain of the enzyme. A conserved motif of the sequence HDXXHXX has been identified in the catalytic domain of all cyclic nucleotide phosphodiesterases isolated to date. The cyclic nucleotide phosphodiesterases within each family display about 65% amino acid homology and the similarity drops to less than 40% when compared between different families with most of the similarity occurring in the catalytic domains.

Most cyclic nucleotide phosphodiesterase genes have more than one alternatively spliced mRNA transcribed from them and in many cases the alternative splicing appears to be highly tissue specific, providing a mechanism for selective expression of different cyclic nucleotide phosphodiesterases (Beavo supra). Cell-type-specific expression suggests that the different isozymes are likely to have different cell-type-specific properties.

Type 1 cyclic nucleotide phosphodiesterases are $Ca^{2+}$/calmodulin dependent, are reported to contain three different genes, each of which appears to have at least two different splice variants, and have been found in the lung, heart and brain. Some of the calmodulin-dependent phosphodiesterases are regulated in vitro by phosphorylation/dephosphorylation events. The effect of phosphorylation is to decrease the affinity of the enzyme for calmodulin, which decreases phosphodiesterase activity, thereby increasing the steady state level of cAMP. Type 2 cyclic nucleotide phosphodiesterases are cGMP-stimulated, are localized in the brain and are thought to mediate the effects of cAMP on catecholamine secretion. Type 3 cyclic nucleotide phosphodiesterases are cGMP-inhibited, have a high specificity for cAMP as a substrate, are one of the major phosphodiesterase isozymes present in vascular smooth muscle, and play a role in cardiac function. One isozyme of type 3 is regulated by one or more insulin-dependent kinases. Type 4 cyclic nucleotide phosphodiesterases are the predominant isoenzyme in most inflammatory cells, with some of the members being activated by cAMP-dependent phosphorylation. Type 5 cyclic nucleotide phosphodiesterases have traditionally been thought of as regulators of cGMP function but may also affect cAMP function. High levels of type 5 cyclic nucleotide phosphodiesterases are found in most smooth muscle preparations, platelets and kidney. Type 6 cyclic nucleotide phosphodiesterase family members play a role in vision and are regulated by light and cGMP. A Type 7 cyclic nucleotide phosphodiesterase family member is found in high concentrations in skeletal muscle. A listing of cyclic nucleotide phosphodiesterase families 1–7, their localization and physiological role is given in Beavo supra, incorporated herein, for that teaching. A Type 8 family is reported in U.S. Pat. No. 5,798,246.

Many functions of the immune and inflammatory response system are inhibited by agents that increase intracellular levels of cAMP (Verghese (1995) *Mol. Pharmacol.* 47:1164–1171). The metabolism of cGMP is involved in smooth muscle, lung and brain cell function (Thompson W. (1991) *Pharma. Ther.* 51:13–33). A variety of diseases have been attributed to increased cyclic nucleotide phosphodiesterase activity which results in decreased levels of cyclic nucleotides. For example, one form of diabetes insipidus in the mouse has been associated with increased phosphodiesterase Family 4 activity and an increase in low-$K_m$ cAMP phosphodiesterase activity has been reported in leukocytes of atopic patients. Defects in cyclic nucleotide phosphodiesterases have also been associated with retinal disease. Retinal degeneration in the rd mouse, human autosomal recessive retinitis pigmentosa, and rod/cone dysplasia 1 in Irish setter dogs has been attributed to mutations in the Family 6 phosphodiesterase, gene B. Family 3 phosphodiesterase has been associated with cardiac disease.

Many inhibitors of different cyclic nucleotide phosphodiesterases have been identified and some have undergone clinical evaluation. For example, Family 3 phosphodiesterase inhibitors are being developed as antithrombotic agents, as antihypertensive agents and as cardiotonic agents useful in the treatment of congestive heart failure. Rolipram, a Family 4 phosphodiesterase inhibitor, has been used in the treatment of depression and other inhibitors of Family 4 phosphodiesterase are undergoing evaluation as anti-inflammatory agents. Rolipram has also been shown to inhibit lipopolysaccharide (LPS)-induced TNF alpha which has been shown to enhance HIV-1 replication in vitro. Therefore, rolipram may inhibit HIV-1 replication (Angel et al. (1995) *AIDS* 9:1137–44). Additionally, based on its ability to suppress the production of TNF alpha and beta and interferon gamma, rolipram has been shown to be effective in the treatment of encephalomyelitis, the experimental animal model for multiple sclerosis (Sommer et al. (1995) *Nat. Med.* 1:244–248) and may be effective in the treatment of tardive dyskinesia (Sasaki et al. (1995) *Eur. J. Pharmacol.* 282:72–76).

There are also nonspecific phosphodiesterase inhibitors such as theophylline, used in the treatment of bronchial asthma and other respiratory diseases, and pentoxifylline, used in the treatment of intermittent claudication and diabetes-induced peripheral vascular disease. Theophylline is thought to act on airway smooth muscle function as well as in an anti-inflammatory or immunomodulatory capacity in the treatment of respiratory diseases (Banner et al. (1995) *Eur. Respir. J* 8:996–1000) where it is thought to act by inhibiting both cyclic nucleotide phosphodiesterase cAMP and cGMP hydrolysis (Banner et al. (1995) *Monaldi Arch. Chest Dis.* 50:286–292). Pentoxifylline, also known to block TNF alpha production, may inhibit HIV-1 replication (Angel et al. supra). A list of cyclic nucleotide phosphodiesterase inhibitors is given in Beavo supra, incorporated herein for that teaching.

Cyclic nucleotide phosphodiesterases have also been reported to affect cellular proliferation in a variety of cell types and have been implicated in the treatment of various cancers. (Bang et al. (1994) *Proc. Natl. Acad. Sci. USA* 91:5330–5334) reported that the prostate carcinoma cell lines DU 145 and LNCaP were growth-inhibited by delivery of cAMP derivatives and phosphodiesterase inhibitors and observed a permanent conversion in phenotype from epithelial to neuronal morphology; Matousovic et al. ((1995) *J. Clin. Invest.* 96:401–410) suggest that cyclic nucleotide phosphodiesterase isozyme inhibitors have the potential to regulate mesangial cell proliferation; Joulain et al. ((1995) *J. Mediat. Cell Signal* 11:63–79) reports that cyclic nucleotide phosphodiesterase has been shown to be an important target involved in the control of lymphocyte proliferation; and Deonarain et al. ((1994) *Brit. J. Cancer* 70:786–94) suggest a tumor targeting approach to cancer treatment that involves intracellular delivery of phosphodiesterases to particular cellular compartments, resulting in cell death.

Accordingly, cyclic nucleotide phosphodiesterases are a major target for drug action and development. Accordingly, it is valuable to the field of pharmaceutical development to identify and characterize tissues and disorders in which cyclic phosphodiesterases are differentially expressed. The present invention advances the state of the art by providing tissues and disorders in which expression of a human cyclic nucleotide phosphodiesterase is relevant. Accordingly, the invention provides methods directed to expression of the phosphodiesterase.

SUMMARY OF THE INVENTION

It is an object of the invention to identify tissues and disorders in which expression of the cyclic nucleotide phosphodiesterase is relevant.

It is a further object of the invention to provide methods wherein the cyclic nucleotide phosphodiesterase polypeptides are useful as reagents or targets in phosphodiesterase assays applicable to treatment and diagnosis of disorders mediated by or related to the cyclic nucleotide phosphodiesterase.

It is a further object of the invention to provide methods wherein polynucleotides corresponding to the phosphodiesterase polypeptide are useful as targets or reagents in phosphodiesterase assays applicable to treatment and diagnosis of disorders mediated by or related to the phosphodiesterase.

A specific object of the invention is to identify compounds that act as agonists and antagonists and modulate the expression of the phosphodiesterase in specific tissues and disorders.

A further specific object of the invention is to provide compounds that modulate expression of the phosphodiesterase for treatment and diagnosis of phosphodiesterase-mediated or related disorders.

The invention is thus based on the expression of a human cyclic nucleotide phosphodiesterase in specific tissues and disorders.

The invention provides methods of screening for compounds that modulate expression or activity of the phosphodiesterase polypeptides or nucleic acid (RNA or DNA) in the specific tissues or disorders.

The invention also provides a process for modulating phosphodiesterase polypeptide or nucleic acid expression or activity, especially using the screened compounds.

Modulation may be used to treat conditions related to aberrant activity or expression of the phosphodiesterase polypeptides or nucleic acids.

The invention also provides assays for determining the activity of or the presence or absence of the phosphodiesterase polypeptides or nucleic acid molecules in specific biological samples, including for disease diagnosis.

The invention also provides assays for determining the presence of a mutation in the polypeptides or nucleic acid molecules, including for disease diagnosis.

The invention utilizes isolated phosphodiesterase polypeptides, including a polypeptide having the amino acid sequence shown in SEQ ID NO 1.

The invention also utilizes an isolated phosphodiesterase nucleic acid molecule having the sequence shown in SEQ ID NO 2.

The invention also utilizes variant polypeptides having an amino acid sequence that is substantially homologous to the amino acid sequence shown in SEQ ID NO 1.

The invention also utilizes variant nucleic acid sequences that are substantially homologous to the nucleotide sequence shown in SEQ ID NO 2.

The invention also utilizes fragments of the polypeptide shown in SEQ ID NO 1 and nucleotide sequence shown in SEQ ID NO 2, as well as substantially homologous fragments of the polypeptide or nucleic acid.

The invention further utilizes nucleic acid constructs comprising the nucleic acid molecules described herein. In a preferred embodiment, the nucleic acid molecules of the invention are operatively linked to a regulatory sequence.

The invention also utilizes vectors and host cells that express the phosphodiesterase and provides methods for expressing the phosphodiesterase nucleic acid molecules and polypeptides in specific cell types and disorders, and particularly recombinant vectors and host cells.

The invention also utilizes methods of making the vectors and host cells and provides methods for using them to assay expression and cellular effects of expression of the phosphodiesterase nucleic acid molecules and polypeptides in specific cell types and disorders.

The invention also utilizes antibodies or antigen-binding fragments thereof that selectively bind the phosphodiesterase polypeptides and fragments.

DESCRIPTION OF THE DRAWINGS

FIGS. 1A–C show the phosphodiesterase nucleotide sequence (SEQ ID NO 2) and the deduced amino acid sequence (SEQ ID NO 1). BLAST analysis showed the top BLAST scores to AB020593, AF127479, AF127480 human dual specificity cAMP/cGMP, and mouse PDE10A, AF110507. AF110507, AF127480, AF127479, AB020593= GenBank accession. See, for example, Sonderling, et al., *Proc. Natl'l. Acad. Sci. U.S.A.* 96:7071–7076 (1999).

amphipathic regions; flexible regions; antigenic index; and surface probability plot.

FIGS. 4A–C show an analysis of the phosphodiesterase open reading frame for amino acids corresponding to specific functional sites. Glycosylation sites are shown in the figure with the actual modified residue being the first amino acid. Protein kinase C phosphorylation sites are shown in the figure with the actual modified residue being the first amino acid. Casein kinase II phophorylation sites are shown in the figure with the actual modified residue being the first amino acid. Tyrosine kinase phosphorylation sites are shown in the figure with the actual modified residue being the last amino acid. N-myristoylation sites are shown in the figure. In addition, amino acids corresponding to the phosphodiesterase signature, HDXXHXX, are found in the sequence HDLDHRG at amino acids 553–559.

Figure 5:
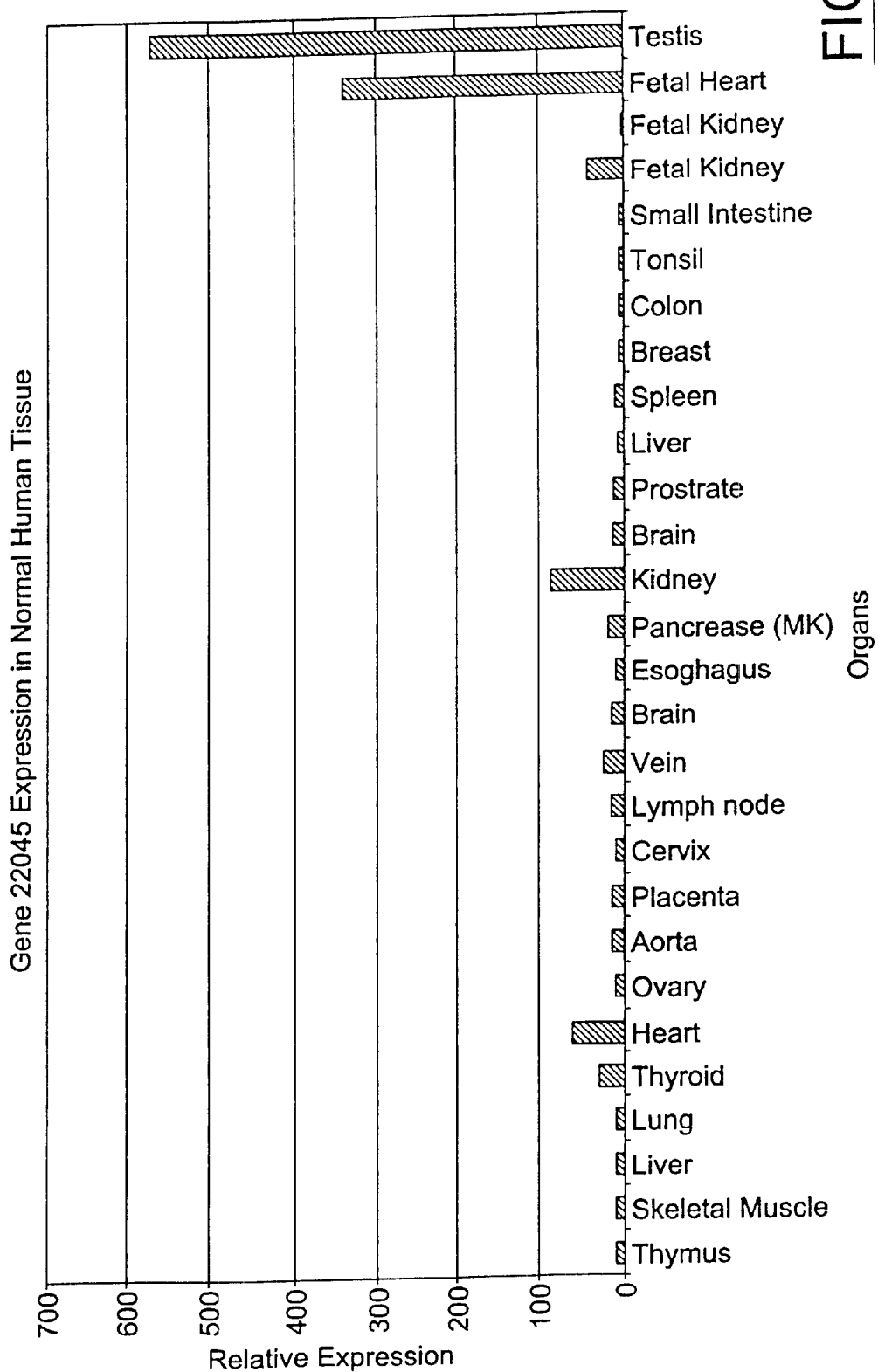

FIG. 5 shows expression of the 22045 phosphodiesterase in various normal human tissues.

Figure 6:
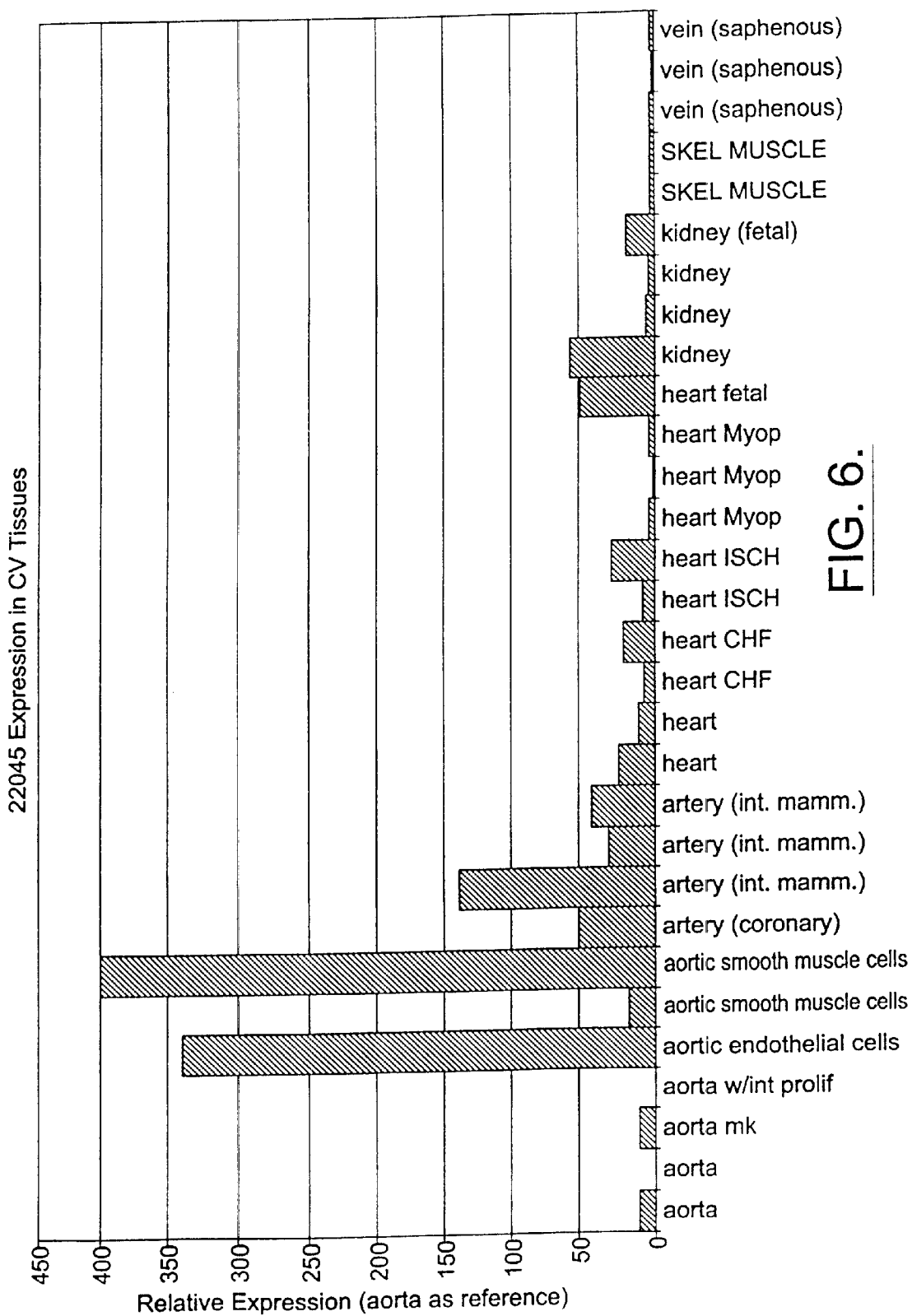

FIG. 6 shows expression of the 22045 phosphodiesterase in various cardiovascular tissues. Int. Mamm.: internal mammary artery; CHF: congestive heart failure; ISCH: ischemic heart; myop: myopathic heart.

Figure 7A:
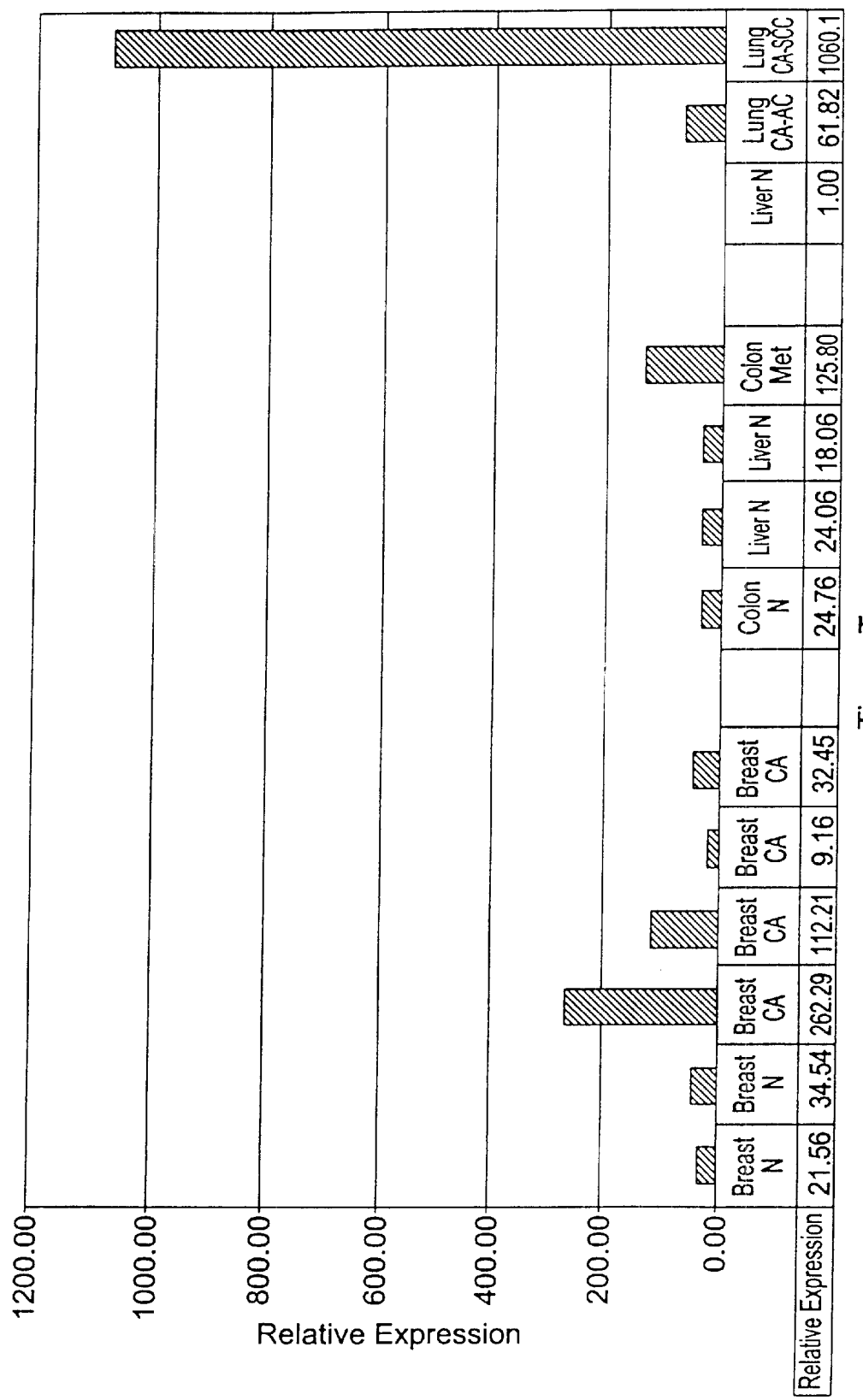
Figure 7B:
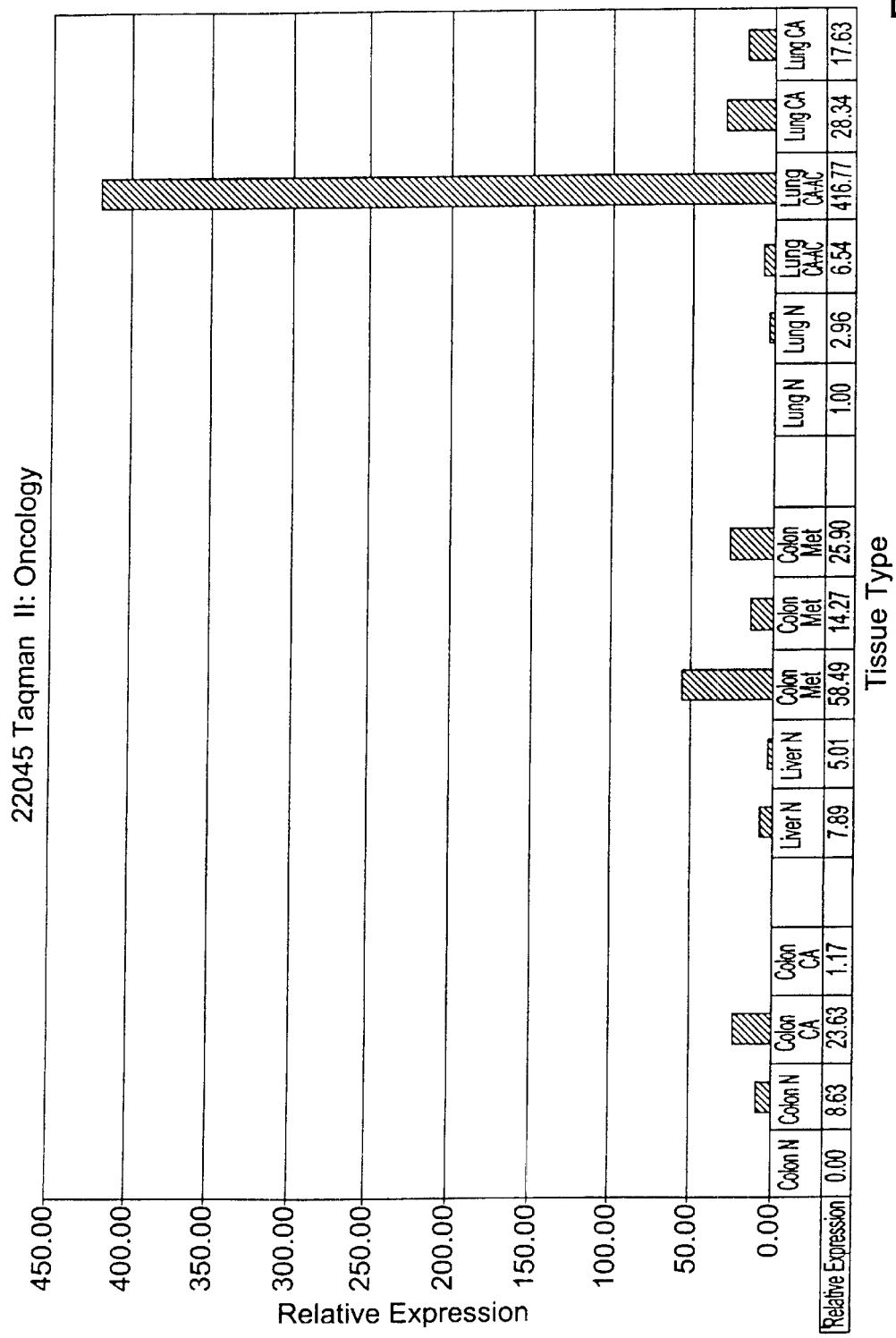

FIGS. 7A and 7B show expression of the phosphodiesterase in breast, lung, and colon carcinoma as well as colon metastases to the liver.

DETAILED DESCRIPTION OF THE INVENTION

As used herein, a "signaling pathway" refers to the modulation (e.g., stimulation or inhibition) of a cellular function/activity upon the binding of a ligand to a receptor. Examples of such functions include mobilization of intracellular molecules that participate in a signal transduction pathway, e.g., phosphatidylinositol 4,5-bisphosphate ($PIP_2$), inositol 1,4,5-triphosphate ($IP_3$) and adenylate cyclase; polarization of the plasma membrane; production or secretion of molecules; alteration in the structure of a cellular component; cell proliferation, e.g., synthesis of DNA; cell migration; cell differentiation; and cell survival.

The response depends on the type of cell. In some cells, binding of a ligand to the receptor may stimulate an activity such as release of compounds, gating of a channel, cellular adhesion, migration, differentiation, etc., through phosphatidylinositol or cyclic AMP metabolism and turnover while in other cells, binding will produce a different result.

The cAMP turnover pathway is a signaling pathway. As used herein, "cyclic AMP turnover and metabolism" refers to the molecules involved in the turnover and metabolism of cAMP as well as to the activities of these molecules. Cyclic AMP is a second messenger produced in response to ligand-induced stimulation of certain receptors. In the cAMP signaling pathway, binding of a ligand can lead to the activation of the enzyme adenyl cyclase, which catalyzes the synthesis of cAMP. The newly synthesized cAMP can in turn activate a cAMP-dependent protein kinase. This activated kinase can phosphorylate a voltage-gated potassium channel protein, or an associated protein, and lead to the inability of the potassium channel to open during an action potential. The inability of the potassium channel to open results in a decrease in the outward flow of potassium, which normally repolarizes the membrane of a neuron, leading to prolonged membrane depolarization.

The cGMP turnover pathway is also a signaling pathway. As used herein, "cyclic GMP turnover and metabolism" refers to the molecules involved in the turnover and metabolism of cGMP as well as to the activities of these molecules. Cyclic GMP is a second messenger produced in response to ligand-induced stimulation of certain receptors. In the cGMP signaling pathway, binding of a ligand can lead to the activation of the enzyme guanyl cyclase, which catalyzes the synthesis of cGMP. Synthesized cGMP can in turn activate a cGMP-dependent protein kinase.

The invention is directed to methods, uses and reagents applicable to methods and uses that are applied to cells, tissues and disorders of these cells and tissues wherein phosphodiesterase expression is relevant. The phosphodiesterase is expressed in a variety of tissues as shown in FIGS. 5 and 6. Accordingly, the methods and uses of the invention as disclosed in greater detail below apply to these tissues, disorders involving these tissues, and particularly to the disorders with which gene expression is associated, as shown in these figures and as disclosed herein. Accordingly, the methods, uses and reagents disclosed in greater detail below especially apply to breast, lung, colon carcinoma, and colonic metastases to the liver, especially apply also to expression in thyroid, heart, kidney, fetal kidney, fetal heart and testes, especially apply to diseased heart and associated vessels, specifically to endothelial cells and vascular smooth muscle cells, applying particularly to congestive heart failure and ischemia. In situ hybridization shows 22045 expression is moderate to low in normal and tumor lung samples, specifically in the large vessels, macrophages, and tumor cells. It also shows low positive expression in normal and diseased heart, specifically in the endothelial and vascular smooth muscle cells. Accordingly, the uses, reagents and methods disclosed in detail herein below apply especially to these tissues, cell types, and disorders.

Methods of Using the Polypeptide

The invention provides methods using the cyclic nucleotide phosphodiesterase, variants, or fragments, including but not limited to use in the cells, tissues, and disorders as disclosed herein.

The invention provides biological assays related to cyclic nucleotide phosphodiesterases. Such assays involve any of the known functions or activities or properties useful for diagnosis and treatment of cyclic phosphodiesterase-related conditions. These include, but are not limited to, hydrolysis of cAMP and cGMP, ability to be bound by specific antibody, cGMP or cAMP binding, and protein kinase A interaction as well as the various other properties and functions disclosed herein and disclosed in the references cited herein.

The invention provides drug screening assays, in cell-based or cell-free systems. Cell-based systems can be native, i.e., cells that normally express the phosphodiesterase, as a biopsy, or expanded in cell culture. In one embodiment, cell-based assays involve recombinant host cells expressing the phosphodiesterase. Accordingly, cells that are useful in this regard include, but are not limited to, those disclosed herein as expressing or differentially expressing the phosphdiesterase, such as those shown in FIGS. 5–7. These include, but are not limited to, cells or tissues derived from heart, kidney, testis, aortic endothelial cells, aortic smooth muscle cells, cells derived from the internal mammary artery, lung small cell carcinoma, breast carcinoma, colon carcinoma, and colon metastases in the liver. Such cells can naturally express the gene or can be recombinant, containing one or more copies of exogenously-introduced phosphodiesterase sequences or genetically modified to modulate expression of the endogenous phosphodiesterase sequence.

This aspect of the invention particularly relates to cells derived from subjects with disorders involving the tissues in which the phosopodiesterase is expressed or derived from tissues subject to disorders including, but not limited to, those disclosed herein. These disorders may naturally occur, as in populations of human subjects, or may occur in model systems such as in vitro systems or in vivo, such as in non-human transgenic organisms, particularly in non-human transgenic animals.

Such assays can involve the identification of agents that interact with the phosphodiesterase protein. This interaction can be detected by functional assays, such as the ability to be affected by an effector molecule, such as phosphorylation by an effector or phosphorylating a substrate. Such interaction can also be measured by ultimate biological effects, such as increasing or decreasing the levels of cAMP or cGMP or having biological effects on immunity/inflammation or cell proliferation, i.e., any of the effects of modulating the intracelluar levels of the second messengers cAMP and cGMP.

Determining the ability of the test compound to interact with the phosphodiesterase can also comprise determining the ability of the test compound to preferentially bind to the polypeptide as compared to the ability of a known binding molecule (e.g., a GMP or cAMP) to bind to the polypeptide.

In yet another aspect of the invention, the invention provides methods to identify proteins that interact with the phosphodiesterase in the tissues and disorders disclosed. The proteins of the invention can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO 94/10300), to identify other proteins (captured proteins) which bind to or interact with the proteins of the invention and modulate their activity.

The invention provides methods to identify compounds that modulate phosphodiesterase activity. Such compounds, for example, can increase or decrease affinity or rate of binding to cGMP or cAMP, compete with cGMP or cAMP for binding to the phosphodiesterase, or displace cGMP or cAMP bound to the phosphodiesterase. Both phosphodiesterase and appropriate variants and fragments can be used in high-throughput screens to assay candidate compounds for the ability to bind to the phosphodiesterase. These compounds can be further screened against a functional phosphodiesterase to determine the effect of the compound on the phosphodiesterase activity. Compounds can be identified that activate (agonist) or inactivate (antagonist) the phosphodiesterase to a desired degree. Modulatory methods can be performed in vitro (e.g., by culturing the cell with the agent) or, alternatively, in vivo (e.g., by administering the agent to a subject. The subject can be a human subject, for example, a subject in a clinical trial or undergoing treatment or diagnosis, or a non-human transgenic subject, such as a transgenic animal model for disease.

The invention provides methods to screen a compound for the ability to stimulate or inhibit interaction between the phosphodiesterase protein and a target molecule that normally interacts with the phosphodiesterase protein. The target can be a cyclic nucleotide or another component of the signal pathway with which the phosphodiesterase protein normally interacts (for example, protein kinase A or other interactor involved in cAMP or cGMP turnover). The assay includes the steps of combining the phosphodiesterase protein with a candidate compound under conditions that allow the phosphodiesterase protein or fragment to interact with the target molecule, and to detect the formation of a complex between the phosphodiesterase protein and the target, or to detect the biochemical consequence of the interaction with the phosphodiesterase and the target, such as any of the associated effects of signal transduction such as protein kinase A phosphorylation, cAMP or cGMP turnover, and biological endpoints of the pathway.

Determining the ability of the phosphodiesterase to bind to a target molecule can also be accomplished using a technology such as real-time Bimolecular Interaction Analysis (BIA). Sjolander et al. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) *Anticancer Drug Des.* 12:145).

Examples of methods for the synthesis of molecular libraries can be found in the art, for example in DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233. Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223, 409), spores (Ladner U.S. Pat. No. '409), plasmids (Cull et al. (1992) *Proc. Natl. Acad. Sci. USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 97:6378–6382); (Felici (1991) *J. Mol. Biol.* 222:301–310); (Ladner supra).

Candidate compounds include, for example, 1) peptides such as soluble peptides, including Ig-tailed fusion peptides and members of random peptide libraries (see, e.g., Lam et al. (1991) *Nature* 354:82–84; Houghten et al. (1991) *Nature* 354:84–86) and combinatorial chemistry-derived molecular libraries made of D- and/or L-configuration amino acids; 2) phosphopeptides (e.g., members of random and partially degenerate, directed phosphopeptide libraries, see, e.g., Songyang et al. (1993) *Cell* 72:767–778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble full-length phosphodiesterase or fragment that competes for cGMP or cAMP binding. Other candidate compounds include mutant phosphodiesterases or appropriate fragments containing mutations that affect phosphodiesterase function and thus compete for cGMP or cAMP. Accordingly, a fragment that competes for cAMP or cGMP, for example with a higher affinity, or a fragment that binds cAMP or cGMP but does not hydrolyze it, is encompassed by the invention.

The invention provides other end points to identify compounds that modulate (stimulate or inhibit) phosphodiesterase activity. The assays typically involve an assay of events in the signal transduction pathway that indicate phosphodiesterase activity. Thus, the expression of genes that are up- or down-regulated in response to the phosphodiesterase dependent signal cascade can be assayed. In one embodiment, the regulatory region of such genes can be operably linked to a marker that is easily detectable, such as luciferase. Alternatively, phosphorylation of the phosphodiesterase, or a phosphodiesterase target, could also be measured.

Any of the biological or biochemical functions mediated by the phosphodiesterase can be used as an endpoint assay. These include all of the biochemical or biochemical/biological events described herein, in the references cited herein, incorporated by reference for these endpoint assay targets, and other functions known to those of ordinary skill in the art.

In the case of the phosphodiesterase, specific end points can include cAMP and cGMP hydrolysis and a decrease in protein kinase A activation.

Assays for phosphodiesterase function include, but are not limited to, those that are well known in the art and available to the person of ordinary skill in the art, for example, those found in Soderling et al., (*Proc. Nat'l Acad. Sci. U.S.A.* 96:7071–7076 (1999), for example, page 7072, which also discloses cGMP-binding assays. Assays for phosphodiesterase function are also disclosed in U.S. Pat. Nos. 5,798,246; 5,581,784; 5,702,936, all of which are incorporated by reference for these assays. Assays are also disclosed in Houslay et al. (1997), *TIBS* 22:217–224, Bloom et al. (1996), *Proc. Natl. Acad. Sci, USA* 93:14188–14192, Zhu et al. (1997) *J. Biol. Chem.* 272:16152–16157, and Beavo (1995), *Physiological Reviews* 75:725–748, also incorporated by reference for these assays.

Binding and/or activating compounds can also be screened by using chimeric phosphodiesterase proteins in which one or more domains, sites, and the like, as disclosed herein, or parts thereof, can be replaced by their heterologous counterparts derived from other phosphodiesterase isoforms of the same family or from phosphodiesterase isoforms of any other phosphodiesterase family. For example, a catalytic region can be used that interacts with a different cyclic nucleotide specificity and/or affinity than the native phosphodiesterase. Accordingly, a different set of signal transduction components is available as an end-point assay for activation. Alternatively, a heterologous targeting sequence can replace the native targeting sequence. This will result in different subcellular or cellular localization and accordingly can result in having an effect on a different signal transduction pathway. Accordingly, a different set of signal transduction components is available as an endpoint assay for activation. As a further alternative, the site of modification by an effector protein, for example phosphorylation by protein kinase A, can be replaced with the site from a different effector protein. This could also provide the use of a different signal transduction pathway for endpoint determination. Activation can also be detected by a reporter gene containing an easily detectable coding region operably linked to a transcriptional regulatory sequence that is part of the native signal transduction pathway.

The invention provides competition binding assays designed to discover compounds that interact with the phosphodiesterase. Thus, a compound is exposed to a phosphodiesterase polypeptide under conditions that allow the compound to bind or to otherwise interact with the polypeptide. Soluble phosphodiesterase polypeptide is also added to the mixture. If the test compound interacts with the soluble phosphodiesterase polypeptide, it decreases the amount of complex formed or activity from the phosphodiesterase target. This type of assay is particularly useful in cases in which compounds are sought that interact with specific regions of the phosphodiesterase. Thus, the soluble polypeptide that competes with the target phosphodiesterase region is designed to contain peptide sequences corresponding to the region of interest.

Another type of competition-binding assay can be used to discover compounds that interact with specific functional sites. As an example, protein kinase A and a candidate compound can be added to a sample of the phosphodiesterase. Compounds that interact with the phosphodiesterase at the same site as the protein kinase A will reduce the amount of complex formed between the phosphodiesterase and protein kinase A. Accordingly, it is possible to discover a compound that specifically prevents interaction between the phosphodiesterase and protein kinase A. Another example involves adding a candidate compound to a sample of phosphodiesterase and cAMP or cGMP. A compound that competes with cAMP or cGMP will reduce the amount of hydrolysis or binding of the cAMP or cGMP to the phosphodiesterase. Accordingly, compounds can be discovered that directly interact with the phosphodiesterase and compete with cAMP or cGMP. Such assays can involve any other component that interacts with the phosphodiesterase.

To perform cell-free drug screening assays, it is desirable to immobilize either the phosphodiesterase, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/phosphodiesterase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes is dissociated. Alternatively, the complexes can be dissociated from the matrix, separated by SDS-PAGE, and the level of phosphodiesterase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a phosphodiesterase-binding target component, such as cAMP or protein kinase A, and a candidate compound are incubated in the phosphodiesterase-presenting wells and the amount of complex trapped in the well can be quantitated. Methods for detecting such complexes, in addition to those described above for the GST-immobilized complexes, include immunodetection of complexes using antibodies reactive with the phosphodiesterase target molecule, or which are reactive with phosphodiesterase and compete with the target molecule; as well as enzyme-linked assays which rely on detecting an enzymatic activity associated with the target molecule.

Modulators of phosphodiesterase level or activity identified according to these assays can be used to test the effects of modulation of expression of the enzyme on the outcome of clinically relevant disorders. This can be accomplished in vitro, in vivo, such as in human clinical trials, and in test models derived from other organisms, such as non-human transgenic subjects. Modulation in such subjects includes, but is not limited to, modulation of the cells, tissues, and disorders particularly disclosed herein. Modulators of phosphodiesterase activity identified according to these drug screening assays can be used to treat a subject with a disorder mediated by the phosphodiesterase pathway, by treating cells that express the phosphodiesterase, such as those disclosed herein, especially in FIGS. 5–7, as well as those disorders disclosed in the references cited herein above. In one embodiment, the cells that are treated are derived from heart, kidney, testes, and thyroid, and as such, modulation is particularly relevant to disorders involving these tissues. In another embodiment, modulation is in aortic endothelial cells, aortic smooth muscle cells and cells of the internal mammary artery. Accordingly, disorders in which modulation is particularly relevant can include these tissues. Since the gene is also over-expressed in breast, lung, and colon carcinoma, modulation is also particularly relevant in these tissues. These methods of treatment include the steps of administering the modulators of phosphodiesterase activity in a pharmaceutical composition as described herein, to a subject in need of such treatment.

Disorders involving the spleen include, but are not limited to, splenomegaly, including nonspecific acute splenitis, congestive spenomegaly, and spenic infarcts; neoplasms, congenital anomalies, and rupture. Disorders associated with splenomegaly include infections, such as nonspecific splenitis, infectious mononucleosis, tuberculosis, typhoid fever, brucellosis, cytomegalovirus, syphilis, malaria, histoplasmosis, toxoplasmosis, kala-azar, trypanosomiasis, schistosomiasis, leishmaniasis, and echinococcosis; congestive states related to partial hypertension, such as cirrhosis of the liver, portal or splenic vein thrombosis, and cardiac failure; lymphohematogenous disorders, such as Hodgkin disease, non-Hodgkin lymphomas/leukemia, multiple myeloma, myeloproliferative disorders, hemolytic anemias, and thrombocytopenic purpura; immunologic-inflammatory conditions, such as rheumatoid arthritis and systemic lupus erythematosus; storage diseases such as Gaucher disease, Niemann-Pick disease, and mucopolysaccharidoses; and other conditions, such as amyloidosis, primary neoplasms and cysts, and secondary neoplasms.

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), *Bronchiolitis obliterans*—organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders involving the liver include, but are not limited to, hepatic injury; jaundice and cholestasis, such as bilirubin and bile formation, hepatic failure and cirrhosis, such as cirrhosis, portal hypertension, including ascites, portosystemic shunts, and splenomegaly; infectious disorders, such as viral hepatitis, including hepatitis A–E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $\alpha_1$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

Disorders involving the uterus and endometrium include, but are not limited to, endometrial histology in the menstrual cycle; functional endometrial disorders, such as anovulatory cycle, inadequate luteal phase, oral contraceptives and induced endometrial changes, and menopausal and post-menopausal changes; inflammations, such as chronic endometritis; adenomyosis; endometriosis; endometrial polyps; endometrial hyperplasia; malignant tumors, such as carcinoma of the endometrium; mixed Müllerian and mesenchymal tumors, such as malignant mixed Müllerian tumors; tumors of the myometrium, including leiomyomas, leiomyosarcomas, and endometrial stromal tumors.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders involving T-cells include, but are not limited to, cell-mediated hypersensitivity, such as delayed type hypersensitivity and T-cell-mediated cytotoxicity, and transplant rejection; autoimmune diseases, such as systemic lupus erythematosus, Sjögren syndrome, systemic sclerosis, inflammatory myopathies, mixed connective tissue disease, and polyarteritis nodosa and other vasculitides; immunologic deficiency syndromes, including but not limited to, primary immunodeficiencies, such as thymic hypoplasia, severe combined immunodeficiency diseases, and AIDS; leukopenia; reactive (inflammatory) proliferations of white cells, including but not limited to, leukocytosis, acute nonspecific lymphadenitis, and chronic nonspecific lymphadenitis; neoplastic proliferations of white cells, including but not limited to lymphoid neoplasms, such as precursor T-cell neoplasms, such as acute lymphoblastic leukemia/lymphoma, peripheral T-cell and natural killer cell neoplasms that include peripheral T-cell lymphoma, unspecified, adult T-cell leukemia/lymphoma, mycosis fungoides and Sézary syndrome, and Hodgkin disease.

Diseases of the skin, include but are not limited to, disorders of pigmentation and melanocytes, including but not limited to, vitiligo, freckle, melasma, lentigo, nevocellular nevus, dysplastic nevi, and malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma; tumors of the dermis, including but not limited to, benign fibrous histiocytoma, dermatofibrosarcoma protuberans, xanthomas, and dermal vascular tumors; tumors of cellular immigrants to the skin, including but not limited to, histiocytosis X, mycosis fungoides (cutaneous T-cell lymphoma), and mastocytosis; disorders of epidermal maturation, including but not limited to, ichthyosis; acute inflammatory dermatoses, including but not limited to, urticaria, acute eczematous dermatitis, and erythema multiforme; chronic inflammatory dermatoses, including but not limited to, psoriasis, lichen planus, and lupus erythematosus; blistering (bullous) diseases, including but not limited to, pemphigus, bullous pemphigoid, dermatitis herpetiformis, and noninflammatory blistering diseases: epidermolysis bullosa and porphyria; disorders of epidermal appendages, including but not limited to, acne vulgaris; panniculitis, including but not limited to, erythema nodosum and erythema induratum; and infection and infestation, such as verrucae, molluscum contagiosum, impetigo, superficial fungal infections, and arthropod bites, stings, and infestations.

In normal bone marrow, the myelocytic series (polymorphoneuclear cells) make up approximately 60% of the cellular elements, and the erythrocytic series, 20–30%. Lymphocytes, monocytes, reticular cells, plasma cells and megakaryocytes together constitute 10–20%. Lymphocytes make up 5–15% of normal adult marrow. In the bone marrow, cell types are add mixed so that precursors of red blood cells (erythroblasts), macrophages (monoblasts), platelets (megakaryocytes), polymorphoneuclear leucocytes (myeloblasts), and lymphocytes (lymphoblasts) can be visible in one microscopic field. In addition, stem cells exist for the different cell lineages, as well as a precursor stem cell for the committed progenitor cells of the different lineages. The various types of cells and stages of each would be known to the person of ordinary skill in the art and are found, for example, on page 42 (FIGS. 2–8) of *Immunology, Imunopathology and Immunity*, Fifth Edition, Sell et al. Simon and Schuster (1996), incorporated by reference for its teaching of cell types found in the bone marrow. According, the invention is directed to disorders arising from these cells. These disorders include but are not limited to the following: diseases involving hematopoetic stem cells; committed lymphoid progenitor cells; lymphoid cells including B and T-cells; committed myeloid progenitors, including monocytes, granulocytes, and megakaryocytes; and committed erythroid progenitors. These include but are not limited to the leukemias, including B-lymphoid leukemias, T-lymphoid leukemias, undifferentiated leukemias; erythroleukemia, megakaryoblastic leukemia, monocytic; [leukemias are encompassed with and without differentiation]; chronic and acute lymphoblastic leukemia, chronic and acute lymphocytic leukemia, chronic and acute myelogenous leukemia, lymphoma, myelo dysplastic syndrome, chronic and acute myeloid leukemia, myelomonocytic leukemia; chronic and acute myeloblastic leukemia, chronic and acute myelogenous leukemia, chronic and acute promyelocytic leukemia, chronic and acute myelocytic leukemia, hematologic malignancies of monocyte-macrophage lineage, such as juvenile chronic myelogenous leukemia; secondary AML, antecedent hematological disorder; refractory anemia; aplastic anemia; reactive cutaneous angioendotheliomatosis; fibrosing disorders involving altered expression in dendritic cells, disorders including systemic sclerosis, E-M syndrome, epidemic toxic oil syndrome, eosinophilic fasciitis localized forms of scleroderma, keloid, and fibrosing colonopathy; angiomatoid malignant fibrous histiocytoma; carcinoma, including primary head and neck squamous cell carcinoma; sarcoma, including kaposi's sarcoma; fibroadanoma and phyllodes tumors, including mammary fibroadenoma; stromal tumors; phyllodes tumors, including histiocytoma; erythroblastosis; neurofibromatosis; diseases of the vascular endothelium; demyelinating, particularly in old lesions; gliosis, vasogenic edema, vascular disease, Alzheimer's and Parkinson's disease; T-cell lymphomas; B-cell lymphomas.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Disorders involving red cells include, but are not limited to, anemias, such as hemolytic anemias, including hereditary spherocytosis, hemolytic disease due to erythrocyte enzyme defects: glucose-6-phosphate dehydrogenase deficiency, sickle cell disease, thalassemia syndromes, paroxysmal nocturnal hemoglobinuria, immunohemolytic anemia, and hemolytic anemia resulting from trauma to red cells; and anemias of diminished erythropoiesis, including megaloblastic anemias, such as anemias of vitamin B12 deficiency: pernicious anemia, and anemia of folate deficiency, iron deficiency anemia, anemia of chronic disease, aplastic anemia, pure red cell aplasia, and other forms of marrow failure.

Disorders involving the thymus include developmental disorders, such as DiGeorge syndrome with thymic hypoplasia or aplasia; thymic cysts; thymic hypoplasia, which involves the appearance of lymphoid follicles within the thymus, creating thymic follicular hyperplasia; and thymomas, including germ cell tumors, lynphomas, Hodgkin disease, and carcinoids. Thymomas can include benign or encapsulated thymoma, and malignant thymoma Type I (invasive thymoma) or Type II, designated thymic carcinoma.

Disorders involving B-cells include, but are not limited to precursor B-cell neoplasms, such as lymphoblastic leukemia/lymphoma. Peripheral B-cell neoplasms include, but are not limited to, chronic lymphocytic leukemia/small lymphocytic lymphoma, follicular lymphoma, diffuse large B-cell lymphoma, Burkitt lymphoma, plasma cell neoplasms, multiple myeloma, and related entities, lymphoplasmacytic lymphoma (Waldenström macroglobulinemia), mantle cell lymphoma, marginal zone lymphoma (MALToma), and hairy cell leukemia.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Disorders of the breast include, but are not limited to, disorders of development; inflammations, including but not limited to, acute mastitis, periductal mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas; tumors including, but not limited to, stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms.

Disorders in the male breast include, but are not limited to, gynecomastia and carcinoma.

Disorders involving the testis and epididymis include, but are not limited to, congenital anomalies such as cryptorchidism, regressive changes such as atrophy, inflammations such as nonspecific epididymitis and orchitis, granulomatous (autoimmune) orchitis, and specific inflammations including, but not limited to, gonorrhea, mumps, tuberculosis, and syphilis, vascular disturbances including torsion, testicular tumors including germ cell tumors that include, but are not limited to, seminoma, spermatocytic seminoma, embryonal carcinoma, yolk sac tumor choriocarcinoma, teratoma, and mixed tumors, tumore of sex cord-gonadal stroma including, but not limited to, leydig (interstitial) cell tumors and sertoli cell tumors (androblastoma), and testicular lymphoma, and miscellaneous lesions of tunica vaginalis.

Disorders involving the prostate include, but are not limited to, inflammations, benign enlargement, for example, nodular hyperplasia (benign prostatic hypertrophy or hyperplasia), and tumors such as carcinoma.

Disorders involving the thyroid include, but are not limited to, hyperthyroidism; hypothyroidism including, but not limited to, cretinism and myxedema; thyroiditis including, but not limited to, hashimoto thyroiditis, subacute (granulomatous) thyroiditis, and subacute lymphocytic (painless) thyroiditis; Graves disease; diffuse and multinodular goiter including, but not limited to, diffuse nontoxic (simple) goiter and multinodular goiter; neoplasms of the thyroid including, but not limited to, adenomas, other benign tumors, and carcinomas, which include, but are not limited to, papillary carcinoma, follicular carcinoma, medullary carcinoma, and anaplastic carcinoma; and cogenital anomalies.

Disorders involving the skeletal muscle include tumors such as rhabdomyosarcoma.

Disorders involving the pancreas include those of the exocrine pancreas such as congenital anomalies, including but not limited to, ectopic pancreas; pancreatitis, including but not limited to, acute pancreatitis; cysts, including but not limited to, pseudocysts; tumors, including but not limited to, cystic tumors and carcinoma of the pancreas; and disorders of the endocrine pancreas such as, diabetes mellitus; islet cell tumors, including but not limited to, insulinomas, gastrinomas, and other rare islet cell tumors.

Disorders involving the small intestine include the malabsorption syndromes such as, celiac sprue, tropical sprue (postinfectious sprue), whipple disease, disaccharidase (lactase) deficiency, abetalipoproteinemia, and tumors of the small intestine including adenomas and adenocarcinoma.

Disorders related to reduced platelet number, thrombocytopenia, include idiopathic thrombocytopenic purpura, including acute idiopathic thrombocytopenic purpura, drug-induced thrombocytopenia, HIV-associated thrombocytopenia, and thrombotic microangiopathies: thrombotic thrombocytopenic purpura and hemolytic-uremic syndrome.

Disorders involving precursor T-cell neoplasms include precursor T lymphoblastic leukemia/lymphoma. Disorders involving peripheral T-cell and natural killer cell neoplasms include T-cell chronic lymphocytic leukemia, large granular lymphocytic leukemia, mycosis fungoides and Sézary syndrome, peripheral T-cell lymphoma, unspecified, angio-immunoblastic T-cell lymphoma, angiocentric lymphoma (NK/T-cell lymphoma$^{4a}$), intestinal T-cell lymphoma, adult T-cell leukemia/lymphoma, and anaplastic large cell lymphoma.

Disorders involving the ovary include, for example, polycystic ovarian disease, Stein-leventhal syndrome, Pseudomyxoma peritonei and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Bone-forming cells include the osteoprogenitor cells, osteoblasts, and osteocytes. The disorders of the bone are complex because they may have an impact on the skeleton during any of its stages of development. Hence, the disorders may have variable manifestations and may involve one, multiple or all bones of the body. Such disorders include, congenital malformations, achondroplasia and thanatophoric dwarfism, diseases associated with abnormal matix such as type 1 collagen disease, osteoporois, paget disease, rickets, osteomalacia, high-turnover osteodystrophy, low-turnover of aplastic disease, osteonecrosis, pyogenic osteomyelitis, tuberculous osteomyelitism, osteoma, osteoid osteoma, osteoblastoma, osteosarcoma, osteochondroma, chondromas, chondroblastoma, chondromyxoid fibroma, chondrosarcoma, fibrous cortical defects, fibrous dysplasia, fibrosarcoma, malignant fibrous histiocytoma, ewing saracoma, primitive neuroectodermal tumor, giant cell tumor, and metastatic tumors.

The invention thus provides methods for treating a disorder characterized by aberrant expression or activity of a phosphodiesterase. In one embodiment, the method involves administering an agent (e.g., an agent identified by a screening assay described herein), or combination of agents that modulates (e.g., upregulates or downregulates) expression or activity of the protein. In another embodiment, the method involves administering the phosphodiesterase as therapy to compensate for reduced or aberrant expression or activity of the protein.

Methods for treatment include but are not limited to the use of soluble phosphodiesterase or fragments of the phosphodiesterase protein that compete for cAMP or cGMP or protein kinase A. These phosphodiesterases or fragments can have a higher affinity for the target so as to provide effective competition.

Stimulation of activity is desirable in situations in which the protein is abnormally downregulated and/or in which increased activity is likely to have a beneficial effect. Likewise, inhibition of activity is desirable in situations in which the protein is abnormally upregulated and/or in which decreased activity is likely to have a beneficial effect. In one example of such a situation, a subject has a disorder characterized by aberrant development or cellular differentiation. In another example, the subject has a proliferative disease (e.g., cancer) or a disorder characterized by an aberrant hematopoietic response. In another example, it is desirable to achieve tissue regeneration in a subject (e.g., where a subject has undergone brain or spinal cord injury and it is desirable to regenerate neuronal tissue in a regulated manner).

The invention also provides methods for diagnosing a disease or predisposition to disease mediated by the phosphodiesterase, including, but not limited to, diseases involving tissues in which the phosphodiesterases are expressed, as disclosed herein, and particularly in heart, thyroid, kidney, testes, aortic endothelial cells, aortic smooth muscle cells, internal mammary artery, breast, lung, and colon carcinoma, especially colonic metastases to the liver. In addition, as indicated in FIG. 6, low positive expression occurs in diseased heart tissue from patients with congestive heart failure and ischemia. In view of these results, in one embodiment of the invention, these disorders are treated by modulating the level or activity of the phosphodieserase gene in diseased hearts. Since expression has been shown (by in situ hybridization) specifically in endothelial cells and vascular smooth muscle cells, treatment is especially directed to these cells. Likewise, in one embodiment, diagnosis is directed to cells and tissues involved in these disorders. As mentioned above, treatment and diagnosis can be in human subjects in which the disease normally occurs and in model systems, both in vitro and in vivo, such as in transgenic animals.

Accordingly, methods are directed to detecting the presence, or levels of, the phosphodiesterase in a cell, tissue, or organism. The methods involve contacting a biological sample with a compound capable of interacting with the phosphodiesterase such that the interaction can be detected.

One agent for detecting phosphodiesterase is an antibody capable of selectively binding to phosphodiesterase. A biological sample includes tissues, cells and biological fluids isolated from a subject, as well as tissues, cells and fluids present within a subject.

The invention also provides methods for diagnosing active disease, or predisposition to disease, in a patient having a variant phosphodiesterase. Thus, phosphodiesterase can be isolated from a biological sample and assayed for the presence of a genetic mutation that results in an aberrant protein. This includes amino acid substitution, deletion, insertion, rearrangement, (as the result of aberrant splicing events), and inappropriate post-translational modification. Analytic methods include altered electrophoretic mobility, altered tryptic peptide digest, altered phosphodiesterase activity in cell-based or cell-free assay, alteration in cAMP or cGMP binding or degradation, protein kinase A binding or phosphorylation, or antibody-binding pattern, altered isoelectric point, direct amino acid sequencing, and any other of the known assay techniques useful for detecting mutations in a protein in general or in a phosphodiesterase specifically.

In vitro techniques for detection of phosphodiesterase include enzyme linked immunosorbent assays (ELISAs), Western blots, immunoprecipitations and immunofluorescence. Alternatively, the protein can be detected in vivo in a subject by introducing into the subject a labeled anti-phosphodiesterase antibody. For example, the antibody can be labeled with a radioactive marker whose presence and location in a subject can be detected by standard imaging techniques. Particularly useful are methods, which detect the allelic variant of the phosphodiesterase expressed in a subject, and methods, which detect fragments of the phosphodiesterase in a sample.

The invention also provides methods of pharmacogenomic analysis including, but not limited to, in the cells, tissues and disorders disclosed herein in which expression of the phosphodiesterase either occurs or shows differential expression. Pharmacogenomics deal with clinically significant hereditary variations in the response to drugs due to altered drug disposition and abnormal action in affected persons. See, e.g., Eichelbaum, M. (1996) Clin. Exp. Pharmacol. Physiol. 23(10–11):983–985, and Linder, M. W. (1997) Clin. Chem. 43(2):254–266. The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes affects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the phosphodiesterase in which one or more of the phosphodiesterase functions in one population is different from those in another population. The polypeptides can be used as a target to ascertain a genetic predisposition that can affect treatment modality. Thus, in a cGMP- or cAMP-based treatment, polymorphism may give rise to catalytic regions that are more or less active. Accordingly, dosage would necessarily be modified to maximize the therapeutic effect within a given population containing the polymorphism. As an alternative to genotyping, specific polymorphic polypeptides could be identified.

The invention also provides for monitoring therapeutic effects during clinical trials and other treatment. Thus, the therapeutic effectiveness of an agent that is designed to increase or decrease gene expression, protein levels or phosphodiesterase activity can be monitored over the course of treatment using the phosphodiesterase polypeptides as an end-point target. The monitoring can be, for example, as follows: (i) obtaining a pre-administration sample from a subject prior to administration of the agent; (ii) detecting the level of expression or activity of the protein in the pre-administration sample; (iii) obtaining one or more post-administration samples from the subject; (iv) detecting the level of expression or activity of the protein in the post-administration samples; (v) comparing the level of expression or activity of the protein in the pre-administration sample with the protein in the post-administration sample or samples; and (vi) increasing or decreasing the administration of the agent to the subject accordingly.

Polypeptides

The methods and uses herein disclosed can be based on polypeptide reagents and targets. The invention is thus based on the use of a human cyclic nucleotide phosphodiesterase. Specifically, an expressed sequence tag (EST) was selected based on homology to phosphodiesterase sequences. This EST was used to design primers based on sequences that it contains and used to identify a cDNA from a fetal testis cDNA library. Positive clones were sequenced and the overlapping fragments were assembled. Analysis of the assembled sequence revealed that the cloned cDNA molecule encodes a cyclic nucleotide phosphodiesterase homologous to GenBank human fetal lung sequence AB020593.

The invention thus relates to expression of a phosphodiesterase having the deduced amino acid sequence shown in FIG. 1 (SEQ ID NO 1).

"Phosphodiesterase polypeptide" or "phosphodiesterase protein" refers to the polypeptide in SEQ ID NO 1. The term "phosphodiesterase protein" or "phosphodiesterase polypeptide", however, further includes the numerous variants described herein, as well as fragments derived from the full-length phosphodiesterases and variants.

Tissues and/or cells in which the phosphodiesterase is found include, but are not limited to those shown in FIGS. 5–7, and particularly in thyroid, heart, kidney, testes, aortic endothelial cells, aortic smooth muscle cells, and internal mammary artery. In addition, the phosphodiesterase is expressed in diseased tissues, including but limited to, heart tissue derived from patients with congestive heart failure and ischemia, and in breast, colon, and lung carcinoma. Expression has been confirmed by Northern blot analysis. In situ hybridization results show moderate to low expression in normal and tumor lung samples, specifically in the large vessels, macrophages, and tumor cells. Furthermore, low positive expression in normal and diseased heart has been shown specifically in the endothelial cells and vascular smooth muscle cells.

The present invention thus utilizes an isolated or purified phosphodiesterase polypeptide and variants and fragments thereof.

As used herein, a polypeptide is said to be "isolated" or "purified" when it is substantially free of cellular material, when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified."

The phosphodiesterase polypeptides can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity.

In one embodiment, the language "substantially free of cellular material" includes preparations of the phosphodiesterase having less than about 30% (by dry weight) other proteins (i.e., contaminating protein), less than about 20% other proteins, less than about 10% other proteins, or less than about 5% other proteins. When the polypeptide is recombinantly produced, it can also be substantially free of culture medium, i.e., culture medium represents less than about 20%, less than about 10%, or less than about 5% of the volume of the protein preparation.

A phosphodiesterase polypeptide is also considered to be isolated when it is part of a membrane preparation or is purified and then reconstituted with membrane vesicles or liposomes.

The language "substantially free of chemical precursors or other chemicals" includes preparations of the phosphodiesterase polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, the phosphodiesterase polypeptide comprises the amino acid sequence shown in SEQ ID NO 1. However, the invention also encompasses sequence variants. Variants include a substantially homologous protein encoded by the same genetic locus in an organism, i.e., an allelic variant.

Variants also encompass proteins derived from other genetic loci in an organism, but having substantial homology to the phosphodiesterase of SEQ ID NO 1. Variants also include proteins substantially homologous to the phosphodiesterase but derived from another organism, i.e., an ortholog. Variants also include proteins that are substantially homologous to the phosphodiesterase that are produced by chemical synthesis. Variants also include proteins that are substantially homologous to the phosphodiesterase that are produced by recombinant methods. It is understood, however, that variants exclude any amino acid sequences disclosed prior to the invention.

As used herein, two proteins (or a region of the proteins) are substantially homologous when the amino acid sequences are at least about 70–75%, typically at least about 80–85%, and most typically at least about 90–95% or more homologous. A substantially homologous amino acid sequence, according to the present invention, will be encoded by a nucleic acid sequence hybridizing to the nucleic acid sequence, or portion thereof, of the sequence shown in SEQ ID NO 2 under stringent conditions as more fully described below.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% or more of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient similarity so as to perform one or more of the same functions performed by the phosphodiesterase. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., *Science* 247:1306–1310 (1990).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |

TABLE 1-continued

Conservative Amino Acid Substitutions.

| | |
|---|---|
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991).

A preferred, non-limiting example of such a mathematical algorithm is described in Karlin et al. (1993) *Proc. Natl. Acad. Sci. USA* 90:5873–5877. Such an algorithm is incorporated into the NBLAST and XBLAST programs (version 2.0) as described in Altschul et al. (1997) *Nucleic Acids Res.* 25:3389–3402. When utilizing BLAST and Gapped BLAST programs, the default parameters of the respective programs (e.g., NBLAST) can be used. See www.ncbi.nlm.nih.gov. In one embodiment, parameters for sequence comparison can be set at score=100, wordlength=12, or can be varied (e.g., W=5 or W=20).

In a preferred embodiment, the percent identity between two amino acid sequences is determined using the Needleman et at. (1970) (*J. Mol. Biol.* 48:444–453) algorithm which has been incorporated into the GAP program in the GCG software package (available at www.gcg.com), using either a BLOSUM 62 matrix or a PAM250 matrix, and a gap weight of 16, 14, 12, 10, 8, 6, or 4 and a length weight of 1, 2, 3,4, 5, or 6. In yet another preferred embodiment, the percent identity between two nucleotide sequences is determined using the GAP program in the GCG software package (Devereux et at. (1984) *Nucleic Acids Res.* 12(1):387) (available at www.gcg.com), using a NWSgapdna.CMP matrix and a gap weight of 40, 50, 60, 70, or 80 and a length weight of 1, 2, 3, 4, 5, or 6.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis et al. (1994) *Comput. Appl. Biosci.* 10:3–5; and FASTA described in Pearson et al. (1988) *PNAS* 85:2444–8.

A variant polypeptide can differ in amino acid sequence by one or more substitutions, deletions, insertions, inversions, fusions, and truncations or a combination of any of these.

Variant polypeptides can be fully functional or can lack function in one or more activities. Thus, in the present case, variations can affect the function, for example, of one or more of the regions corresponding to the conserved catalytic region, carboxyterminal regulatory regions, aminoterminal regulatory regions, aminoterminal targeting regions, regions involved in membrane association, regions involved in enzyme activation, for example, by phosphorylation, and regions involved in interaction with components of the cyclic nucleotide (e.g., AMP, GMP)-dependent signal transduction pathways.

Fully functional variants typically contain only conservative variation or variation in non-critical residues or in non-critical regions. Functional variants can also contain substitution of similar amino acids, which results in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

As indicated, variants can be naturally-occurring or can be made by recombinant means or chemical synthesis to provide useful and novel characteristics for the phosphodiesterase polypeptide. This includes preventing immunogenicity from pharmaceutical formulations by preventing protein aggregation.

Useful variations further include alteration of catalytic activity. For example, one embodiment involves a variation at the binding site that results in binding but not hydrolysis, or slower hydrolysis, of cAMP or cGMP. A further useful variation at the same site can result in altered affinity for cAMP or cGMP. Useful variation includes one that prevents activation by protein kinase A. Another useful variation provides a fusion protein in which one or more domains or subregions are operationally fused to one or more domains or subregions from another phosphodiesterase isoform or family.

Amino acids that are essential for function can be identified by methods known in the art, such as site-directed mutagenesis or alanine-scanning mutagenesis (Cunningham et al. (1985) *Science* 244:1081–1085). The latter procedure introduces single alanine mutations at every residue in the molecule. The resulting mutant molecules are then tested for biological activity, such as cAMP or cGMP hydrolysis in vitro or cGMP- or cAMP-dependent in vitro activity, such as proliferative activity. Sites that are critical for cGMP or cAMP or protein kinase A binding can also be determined by structural analysis such as crystallization, nuclear magnetic resonance or photoaffinity labeling (Smith et al. (1992) *J. Mol. Biol.* 224:899–904; de Vos et al. (1992) *Science* 255:306–312).

Substantial homology can be to the entire nucleic acid or amino acid sequence or to fragments of these sequences.

The invention thus also includes polypeptide fragments of the phosphodiesterase. Fragments can be derived from the amino acid sequence shown in SEQ ID NO 1. However, the invention also encompasses fragments of the variants of the phosphodiesterase as described herein.

Accordingly, a fragment can comprise at least about 10, 15, 20, 25, 30, 35, 40, 45, 50 or more contiguous amino acids. Fragments can retain one or more of the biological activities of the protein, for example the ability to bind to or hydrolyze cGMP or cAMP, as well as fragments that can be used as an immunogen to generate phosphodiesterase antibodies.

Biologically active fragments (peptides which are, for example, 5, 7, 10, 12, 15, 20, 30, 35, 36, 37, 38, 39, 40, 50, 100 or more amino acids in length) can comprise a domain or motif, e.g., catalytic site, phosphodiesterase signature, and sites for glycosylation, protein kinase C phosphorylation, casein kinase II phosphorylation, tyrosine kinase phosphorylation, and N-myristoylation. Further possible fragments include the catalytic site or domain including HDXXHXX, an allosteric binding site, sites important for cellular and subcellular targeting, sites functional for interacting with components of other cGMP or cAMP-dependent signal transduction pathways, and aminoterminal and carboxyterminal regulatory sites.

Such domains or motifs can be identified by means of routine computerized homology searching procedures.

Fragments, for example, can extend in one or both directions from the functional site to encompass 5, 10, 15, 20, 30, 40, 50, or up to 100 amino acids. Further, fragments can include sub-fragments of the specific domains mentioned above, which sub-fragments retain the function of the domain from which they are derived.

These regions can be identified by well-known methods involving computerized homology analysis.

The invention also provides fragments with immunogenic properties. These contain an epitope-bearing portion of the phosphodiesterase and variants. These epitope-bearing peptides are useful to raise antibodies that bind specifically to a phosphodiesterase polypeptide or region or fragment. These peptides can contain at least 10, 12, at least 14, or between at least about 15 to about 30 amino acids.

Figure 2:
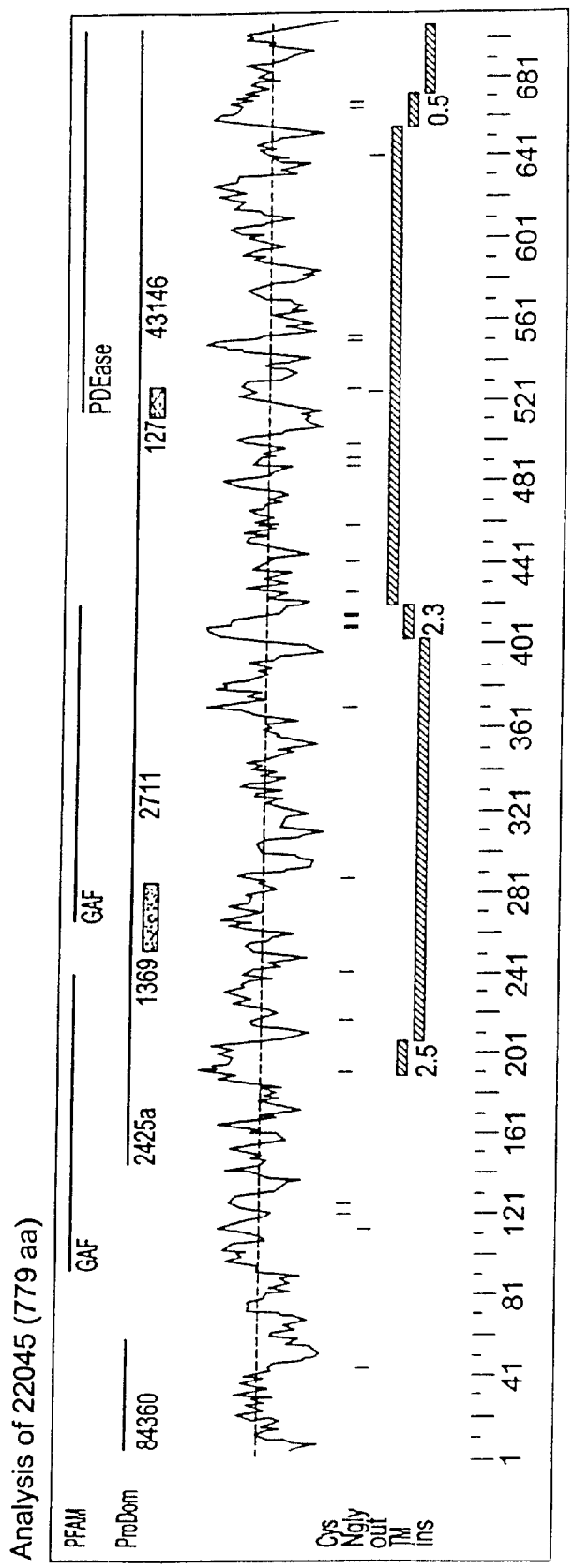
FIG. 2 shows a hydrophobicity plot of the phosphodiesterase.
Figure 3:
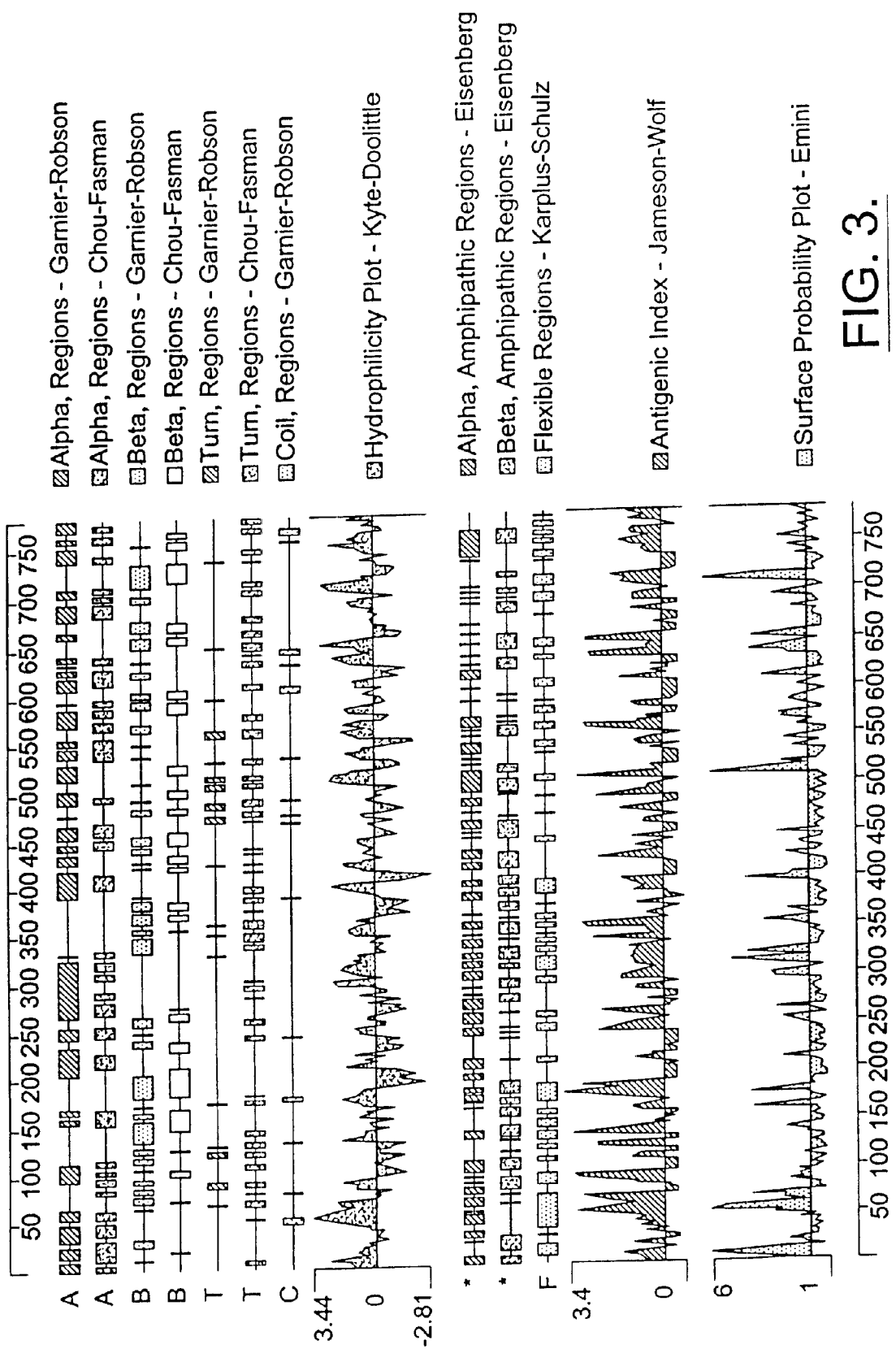
FIG. 3 shows an analysis of the phosphodiesterase amino acid sequence: αβturn and coil regions; hydrophilicity.

Non-limiting examples of antigenic polypeptides that can be used to generate antibodies include but are not limited to peptides derived from an extracellular site. Regions having a high antigenicity index are shown in FIG. 3. However, intracellularly-made antibodies ("intrabodies") are also encompassed, which would recognize intracellular peptide regions.

The epitope-bearing phosphodiesterase polypeptides may be produced by any conventional means (Houghten, R. A. (1985) *Proc. Natl. Acad. Sci. USA* 82:5131–5135). Simultaneous multiple peptide synthesis is described in U.S. Pat. No. 4,631,211.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the phosphodiesterase fragment and an additional region fused to the carboxyl terminus of the fragment.

The invention thus provides chimeric or fusion proteins. These comprise a phosphodiesterase peptide sequence operatively linked to a heterologous peptide having an amino acid sequence not substantially homologous to the phosphodiesterase. "Operatively linked" indicates that the phosphodiesterase peptide and the heterologous peptide are fused in-frame. The heterologous peptide can be fused to the N-terminus or C-terminus of the phosphodiesterase or can be internally located.

In one embodiment the fusion protein does not affect phosphodiesterase function per se. For example, the fusion protein can be a GST-fusion protein in which the phosphodiesterase sequences are fused to the N- or C-terminus of the GST sequences. Other types of fusion proteins include, but are not limited to, enzymatic fusion proteins, for example beta-galactosidase fusions, yeast two-hybrid GAL-4 fusions, poly-His fusions and Ig fusions. Such fusion proteins, particularly poly-His fusions, can facilitate the purification of recombinant phosphodiesterase. In certain host cells (e.g., mammalian host cells), expression and/or secretion of a protein can be increased by using a heterologous signal sequence. Therefore, in another embodiment, the fusion protein contains a heterologous signal sequence at its N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists (Bennett et al. (1995) *J. Mol. Recog.* 8:52–58 (1995) and Johanson et al. *J. Biol. Chem.* 270:9459–9471). Thus, this invention also utilizes soluble fusion proteins containing a phosphodiesterase polypeptide and various portions of the constant regions of heavy or light chains of immunoglobulins of various subclass (IgG, IgM, IgA, IgE). Preferred as immunoglobulin is the constant part of the heavy chain of human IgG, particularly IgG1, where fusion takes place at the hinge region. For some uses it is desirable to remove the Fc after the fusion protein has been used for its intended purpose, for example when the fusion protein is to be used as antigen for immunizations. In a particular embodiment, the Fc part can be removed in a simple way by a cleavage sequence, which is also incorporated and can be cleaved with factor Xa.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al. (1992) *Current Protocols in Molecular Biology*). Moreover, many expression vectors are commercially available that already encode a fusion moiety (e.g., a GST protein). A phosphodiesterase-encoding nucleic acid can be cloned into such an expression vector such that the fusion moiety is linked in-frame to the phosphodiesterase.

Another form of fusion protein is one that directly affects phosphodiesterase functions. Accordingly, a phosphodiesterase polypeptide is encompassed by the present invention in which one or more of the phosphodiesterase domains (or parts thereof) has been replaced by homologous domains (or parts thereof) from another phosphodiesterase family. Accordingly, various permutations are possible. For example, the aminoterminal regulatory domain, or subregion thereof, can be replaced with the domain or subregion from another isoform or phosphodiesterase family. As a further example, the catalytic domain or parts thereof, can be replaced; the carboxyterminal domain or subregion can be replaced. Thus, chimeric phosphodiesterases can be formed in which one or more of the native domains or subregions has been replaced by another.

Additionally, chimeric phosphodiesterase proteins can be produced in which one or more functional sites is derived from a different isoform, or from another phosphodiesterase family. It is understood, however, that sites could be derived from phosphodiesterase families that occur in the mammalian genome but which have not yet been discovered or characterized. Such sites include but are not limited to the catalytic site, aminoterminal regulatory site, carboxyterminal regulatory site, sites important for targeting to subcellular and cellular locations, sites functional for interaction with components of cyclic AMP- and cyclic GMP-dependent signal transduction pathways, protein kinase A phosphorylation sites, glycosylation sites, and other functional sites disclosed herein.

The isolated phosphodiesterases can be purified from cells that naturally express it, such as from those shown in FIGS. 5–7 and/or specifically disclosed herein above, among others, especially purified from cells that have been altered to express it (recombinant), or synthesized using known protein synthesis methods.

In one embodiment, the protein is produced by recombinant DNA techniques. For example, a nucleic acid molecule encoding the phosphodiesterase polypeptide is cloned into an expression vector, the expression vector introduced into a host cell and the protein expressed in the host cell. The protein can then be isolated from the cells by an appropriate purification scheme using standard protein purification techniques.

Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (1990) *Meth. Enzymol.* 182: 626–646) and Rattan et al. (1992) Ann. *N.Y. Acad. Sci.* 663:48–62).

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the aminoterminal residue of polypeptides made in *E. coli,* prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

The same type of modification may be present in the same or varying degree at several sites in a given polypeptide. Also, a given polypeptide may contain more than one type of modification.

Methods of Using Antibodies

Methods for using antibodies as disclosed herein are particularly applicable to the cells, tissues and disorders shown in FIGS. 5–7 and as otherwise discussed herein above.

The invention provides methods using antibodies that selectively bind to the phosphodiesterase and its variants and fragments. An antibody is considered to selectively bind, even if it also binds to other proteins that are not substantially homologous with the phosphodiesterase. These other proteins share homology with a fragment or domain of the phosphodiesterase. This conservation in specific regions gives rise to antibodies that bind to both proteins by virtue of the homologous sequence. In this case, it would be understood that antibody binding to the phosphodiesterase is still selective.

The invention provides methods of using antibodies to isolate a phosphodiesterase by standard techniques, such as affinity chromatography or immunoprecipitation. The antibodies can facilitate the purification of the phosphodiesterase from cells naturally expressing it and cells recombinantly producing it.

The antibodies can be used to detect the presence of phosphodiesterase in cells or tissues to determine the pattern of expression of the phosphodiesterase among various tissues in an organism and over the course of normal development.

The antibodies can be used to detect phosphodiesterase in situ, in vitro, or in a cell lysate or supernatant in order to evaluate the abundance and pattern of expression.

The antibodies can be used to assess abnormal tissue distribution or abnormal expression during development.

Antibody detection of circulating fragments of the full length phosphodiesterase can be used to identify phosphodiesterase turnover.

Further, the antibodies can be used to assess phosphodiesterase expression in disease states such as in active stages of the disease or in an individual with a predisposition toward disease related to phosphodiesterase function. When a disorder is caused by an inappropriate tissue distribution, developmental expression, or level of expression of the phosphodiesterase protein, the antibody can be prepared against the normal phosphodiesterase protein. If a disorder is characterized by a specific mutation in the phosphodiesterase, antibodies specific for this mutant protein can be used to assay for the presence of the specific mutant phosphodiesterase. However, intracellularly-made antibodies ("intrabodies") are also encompassed, which would recognize intracellular phosphodiesterase peptide regions.

The antibodies can also be used to assess normal and aberrant subcellular localization in cells in the various tissues in an organism. Antibodies can be developed against the whole phosphodiesterase or portions of the phosphodiesterase.

The diagnostic uses can be applied, not only in genetic testing, but also in monitoring a treatment modality. Accordingly, where treatment is ultimately aimed at correcting phosphodiesterase expression level or the presence of aberrant phosphodiesterases and aberrant tissue distribution or developmental expression, antibodies directed against the phosphodiesterase or relevant fragments can be used to monitor therapeutic efficacy.

Antibodies accordingly can be used diagnostically to monitor protein levels in tissue as part of a clinical testing procedure, e.g., to, for example, determine the efficacy of a given treatment regimen.

Additionally, antibodies are useful in pharmacogenomic analysis. Thus, antibodies prepared against polymorphic phosphodiesterase can be used to identify individuals that require modified treatment modalities.

Antibodies can also be used in diagnostic procedures as an immunological marker for aberrant phosphodiesterase analyzed by electrophoretic mobility, isoelectric point, tryptic peptide digest, and other physical assays known to those in the art.

The antibodies are also useful for tissue typing. Thus, where the phosphodiesterase is expressed in a specific tissue, antibodies that are specific for this phosphodiesterase can be used to identify the tissue type.

The antibodies are also useful for inhibiting phosphodiesterase function, for example, blocking binding of cGMP or cAMP, protein kinase A, or the catalytic site.

These uses can also be applied in a therapeutic context in which treatment involves inhibiting phosphodiesterase function. Antibodies can be prepared against specific fragments containing sites required for function or against intact phosphodiesterase.

Completely human antibodies are particularly desirable for therapeutic treatment of human patients. For an overview of this technology for producing human antibodies, see Lonberg et al. (1995) *Int. Rev. Immunol.* 13:65–93. For a detailed discussion of this technology for producing human antibodies and human monoclonal antibodies and protocols for producing such antibodies, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806.

The invention also encompasses kits for using antibodies to detect the presence of a phosphodiesterase protein in a biological sample. The kit can comprise antibodies such as a labeled or labelable antibody and a compound or agent for detecting phosphodiesterase in a biological sample; means for determining the amount of phosphodiesterase in the sample; and means for comparing the amount of phosphodiesterase in the sample with a standard. The compound or agent can be packaged in a suitable container. The kit can further comprise instructions for using the kit to detect phosphodiesterase.

Antibodies

The methods for using antibodies described above are based on the generation of antibodies that specifically bind to the phosphodiesterase or its variants or fragments.

To generate antibodies, an isolated phosphodiesterase polypeptide is used as an immunogen to generate antibodies using standard techniques for polyclonal and monoclonal antibody preparation. Either the full-length protein or antigenic peptide fragment can be used. Regions having a high antigenicity index are shown in FIG. 3.

Antibodies are preferably prepared from these regions or from discrete fragments in these regions. However, antibodies can be prepared from any region of the peptide as described herein. A preferred fragment produces an antibody that diminishes or completely prevents cAMP or cGMP hydrolysis or binding. Antibodies can be developed against the entire phosphodiesterase or domains of the phosphodiesterase as described herein. Antibodies can also be developed against specific functional sites as disclosed herein.

The antigenic peptide can comprise a contiguous sequence of at least 12, 14, 15, or 30 amino acid residues. In one embodiment, fragments correspond to regions that are located on the surface of the protein, e.g., hydrophilic regions. These fragments are not to be construed, however, as encompassing any fragments, which may be disclosed prior to the invention.

Antibodies can be polyclonal or monoclonal. An intact antibody, or a fragment thereof (e.g. Fab or F(ab')$_2$) can be used.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

An appropriate immunogenic preparation can be derived from native, recombinantly expressed, or chemically synthesized peptides.

Methods for Using the Polynucleotide

The methods and uses described herein below for the phosphodiesterase polynucleotide are particularly applicable to the cells, tissues, and disorders shown in FIGS. 5–7, and specifically discussed herein above.

The nucleic acid fragments useful to practice the invention provide probes or primers in assays, such as those described herein. "Probes" are oligonucleotides that hybridize in a base-specific manner to a complementary strand of nucleic acid. Such probes include polypeptide nucleic acids, as described in Nielsen et al. (1991) Science 254:1497–1500. Typically, a probe comprises a region of nucleotide sequence that hybridizes under highly stringent conditions to at least about 15, typically about 20–25, and more typically about 40, 50 or 75 consecutive nucleotides of the nucleic acid sequence shown in SEQ ID NO 2 and the complements thereof More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

The phosphodiesterase polynucleotides can be utilized as probes and primers in biological assays.

Where the polynucleotides are used to assess phosphodiesterase properties or functions, such as in the assays described herein, all or less than all of the entire cDNA can be useful. Assays specifically directed to phosphodiesterase functions, such as assessing agonist or antagonist activity, encompass the use of known fragments. Further, diagnostic methods for assessing phosphodiesterase function can also be practiced with any fragment, including those fragments that may have been known prior to the invention. Similarly, in methods involving treatment of phosphodiesterase dysfunction, all fragments are encompassed including those, which may have been known in the art.

The invention utilizes the phosphodiesterase polynucleotides as a hybridization probe for cDNA and genomic DNA to isolate a full-length cDNA and genomic clones encoding variant polypeptides and to isolate cDNA and genomic clones that correspond to variants producing the same polypeptides shown in SEQ ID NO 1 or the other variants described herein. This method is useful for isolating variant genes and cDNA that are expressed in the cells, tissues, and disorders disclosed herein.

The probe can correspond to any sequence along the entire length of the gene encoding the phosphodiesterase. Accordingly, it could be derived from 5' noncoding regions, the coding region, and 3' noncoding regions.

The nucleic acid probe can be, for example, the full-length cDNA of SEQ ID NO 2, or a fragment thereof, such as an oligonucleotide of at least 12, 15, 30, 50, 100, 250 or 500 nucleotides in length and sufficient to specifically hybridize under stringent conditions to mRNA or DNA.

Fragments of the polynucleotides can also be used to synthesize larger fragments or full-length polynucleotides described herein. For example, a fragment can be hybridized to any portion of an mRNA and a larger or full-length cDNA can be produced.

Fragments can also be used to synthesize antisense molecules of desired length and sequence.

Antisense nucleic acids, useful in treatment and diagnosis, can be designed using the nucleotide sequences of SEQ ID NO 2, and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Additionally, the nucleic acid molecules useful to practice the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) Bioorganic & Medicinal Chemistry 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) Proc. Natl. Acad. Sci. USA 93:14670. PNAs can be further modified, e.g., to enhance their stability, specificity or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra, Finn et al. (1996) Nucleic Acids Res. 24(17):3357–63, Mag et al. (1989) Nucleic Acids Res. 17:5973, and Peterser et al. (1975) Bioorganic Med. Chem. Lett. 5:1119.

The nucleic acid molecules and fragments useful to practice the invention can also include other appended groups such as peptides (e.g., for targeting host cell phosphodiesterases in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO 88/0918) or the blood brain barrier (see, e.g., PCT Publication No. WO 89/10134). In addition, oligonucleotides can be modified with hybridization-triggered cleavage agents (see, e.g., Krol et al. (1988) *Bio-Techniques* 6:958–976) or intercalating agents (see, e.g., Zon (1988) *Pharm Res.* 5:539–549).

The phosphodiesterase polynucleotides can also be used as primers for PCR to amplify any given region of a phosphodiesterase polynucleotide.

The phosphodiesterase polynucleotides can also be used to construct recombinant vectors. Such vectors include expression vectors that express a portion of, or all of, the phosphodiesterase polypeptides. Vectors also include insertion vectors, used to integrate into another polynucleotide sequence, such as into the cellular genome, to alter in situ expression of phosphodiesterase genes and gene products. For example, an endogenous phosphodiesterase coding sequence can be replaced via homologous recombination with all or part of the coding region containing one or more specifically introduced mutations.

The phosphodiesterase polynucleotides can also be used to express antigenic portions of the phosphodiesterase protein.

The phosphodiesterase polynucleotides can also be used as probes for determining the chromosomal positions of the phosphodiesterase polynucleotides by means of in situ hybridization methods, such as FISH. (For a review of this technique, see Verma et al. (1988) *Human Chromosomes: A Manual of Basic Techniques* (Pergamon Press, New York), and PCR mapping of somatic cell hybrids. The mapping of the sequence to chromosomes is important in correlating these sequences with genes associated with disease, especially where translocations and/or amplification has occurred.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between a gene and a disease mapped to the same chromosomal region, can then be identified through linkage analysis (co-inheritance of physically adjacent genes), described in, for example, Egeland et al. ((1987) *Nature* 325:783–787).

Moreover, differences in the DNA sequences between individuals affected and unaffected with a disease associated with a specified gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations, that are visible from chromosome spreads, or detectable using PCR based on that DNA sequence. Ultimately, complete sequencing of genes from several individuals can be performed to confirm the presence of a mutation and to distinguish mutations from polymorphisms.

The phosphodiesterase polynucleotide probes can also be used to determine patterns of the presence of the gene encoding the phosphodiesterase with respect to tissue distribution, for example, whether gene duplication has occurred and whether the duplication occurs in all or only a subset of cells in a tissue. The genes can be naturally occurring or can have been introduced into a cell, tissue, or organism exogenously.

The phosphodiesterase polynucleotides can also be used to design ribozymes corresponding to all, or a part, of the mRNA produced from genes encoding the polynucleotides described herein, the ribozymes being useful to treat or diagnose a disorder or otherwise modulate expression of the nucleic acid.

The phosphodiesterase polynucleotides can also be used to make vectors that express part, or all, of the phosphodiesterase polypeptides.

The phosphodiesterase polynucleotides can also be used to construct host cells expressing a part, or all, of the phosphodiesterase polynucleotides and polypeptides.

The phosphodiesterase polynucleotides can also be used to construct transgenic animals expressing all, or a part, of the phosphodiesterase polynucleotides and polypeptides.

The phosphodiesterase polynucleotides can also be used as hybridization probes to determine the level of phosphodiesterase nucleic acid expression. Accordingly, the probes can be used to detect the presence of, or to determine levels of, phosphodiesterase nucleic acid in cells, tissues, and in organisms. DNA or RNA level can be determined. Probes can be used to assess gene copy number in a given cell, tissue, or organism. This is particularly relevant in cases in which there has been an amplification of the phosphodiesterase gene.

Alternatively, the probe can be used in an in situ hybridization context to assess the position of extra copies of the phosphodiesterase gene, as on extrachromosomal elements or as integrated into chromosomes in which the phosphodiesterase gene is not normally found, for example, as a homogeneously staining region.

These uses are relevant for diagnosis of disorders involving an increase or decrease in phosphodiesterase expression relative to normal, such as a proliferative disorder, a differentiative or developmental disorder, or a hematopoietic disorder, such as in the cells and tissues shown in FIGS. 5–7 and otherwise specifically discussed herein. Thus in one embodiment, disorders include diseases of the heart, such as congestive heart failure and ischemia, as well as carcinoma of the lung, breast and colon.

Thus, the present invention provides a method for identifying a disease or disorder associated with aberrant expression or activity of phosphodiesterase nucleic acid, in which a test sample is obtained from a subject and nucleic acid (e.g., mRNA, genomic DNA) is detected, wherein the presence of the nucleic acid is diagnostic for a subject having or at risk of developing a disease or disorder associated with aberrant expression or activity of the nucleic acid.

One aspect of the invention relates to diagnostic assays for determining nucleic acid expression as well as activity in the context of a biological sample (e.g., blood, serum, cells, tissue) to determine whether an individual has a disease or disorder, or is at risk of developing a disease or disorder, associated with aberrant nucleic acid expression or activity. Such assays can be used for prognostic or predictive purpose to thereby prophylactically treat an individual prior to the onset of a disorder characterized by or associated with expression or activity of the nucleic acid molecules.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express the phosphodiesterase, such as by measuring the level of a phosphodiesterase-encoding nucleic acid in a sample of cells from a subject e.g., mRNA or genomic DNA, or determining if the phosphodiesterase gene has been mutated.

Nucleic acid expression assays are useful for drug screening to identify compounds that modulate phosphodiesterase nucleic acid expression (e.g., antisense, polypeptides, peptidomimetics, small molecules or other drugs). A cell is contacted with a candidate compound and the expression of mRNA determined. The level of expression of the mRNA in the presence of the candidate compound is compared to the level of expression of the mRNA in the absence of the candidate compound. The candidate compound can then be identified as a modulator of nucleic acid expression based on this comparison and be used, for example to treat a disorder characterized by aberrant nucleic acid expression. The modulator can bind to the nucleic acid or indirectly modulate expression, such as by interacting with other cellular components that affect nucleic acid expression.

Modulatory methods can be performed in vitro (e.g., by culturing the cell with the agent) or, alternatively, in vivo (e.g., by administering the gene to a subject) in patients or in transgenic animals.

The invention thus provides a method for identifying a compound that can be used to treat a disorder associated with expression of the phosphodiesterase gene. The method typically includes assaying the ability of the compound to modulate the expression of the phosphodiesterase nucleic acid and thus identifying a compound that can be used to treat a disorder characterized by excessive or deficient phosphodiesterase nucleic acid expression.

The assays can be performed in cell-based and cell-free systems, such as systems using the tissues described herein, in which the gene is expressed or in model systems for the disorders to which the invention pertains. Cell-based assays include cells naturally expressing the phosphodiesterase nucleic acid or recombinant cells genetically engineered to express specific nucleic acid sequences.

Alternatively, candidate compounds can be assayed in vivo in patients or in transgenic animals.

The assay for phosphodiesterase nucleic acid expression can involve direct assay of nucleic acid levels, such as mRNA levels, or on collateral compounds involved in the signal pathway (such as cAMP or cGMP turnover). Further, the expression of genes that are up- or down-regulated in response to the phosphodiesterase signal pathway can also be assayed. In this embodiment the regulatory regions of these genes can be operably linked to a reporter gene such as luciferase.

Thus, modulators of phosphodiesterase gene expression can be identified in a method wherein a cell is contacted with a candidate compound and the expression of mRNA determined. The level of expression of phosphodiesterase mRNA in the presence of the candidate compound is compared to the level of expression of phosphodiesterase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

Accordingly, the invention provides methods of treatment, with the nucleic acid as a target, using a compound identified through drug screening as a gene modulator to modulate phosphodiesterase nucleic acid expression. Modulation includes both up-regulation (i.e. activation or agonization) or down-regulation (suppression or antagonization) or effects on nucleic acid activity (e.g. when nucleic acid is mutated or improperly modified). Treatment is of disorders characterized by aberrant expression or activity of the nucleic acid.

The gene is particularly relevant for the treatment of disorders involving the tissues shown in FIGS. 5–7, particularly thyroid, heart, kidney, testes, aortic endothelial cells, aortic smooth muscle cells, internal mammary artery, as well as tissues and cells involved in congestive heart failure and ischemia, and in lung, colon and breast carcinoma.

Alternatively, a modulator for phosphodiesterase nucleic acid expression can be a small molecule or drug identified using the screening assays described herein as long as the drug or small molecule inhibits the phosphodiesterase nucleic acid expression.

The phosphodiesterase polynucleotides are also useful for monitoring the effectiveness of modulating compounds on the expression or activity of the phosphodiesterase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

Monitoring can be, for example, as follows: (i) obtaining a pre-administration sample from a subject prior to administration of the agent; (ii) detecting the level of expression of a specified mRNA or genomic DNA of the invention in the pre-administration sample; (iii) obtaining one or more post-administration samples from the subject; (iv) detecting the level of expression or activity of the mRNA or genomic DNA in the post-administration samples; (v) comparing the level of expression or activity of the mRNA or genomic DNA in the pre-administration sample with the mRNA or genomic DNA in the post-administration sample or samples; and (vi) increasing or decreasing the administration of the agent to the subject accordingly.

The phosphodiesterase polynucleotides can be used in diagnostic assays for qualitative changes in phosphodiesterase nucleic acid, and particularly in qualitative changes that lead to pathology. The polynucleotides can be used to detect mutations in phosphodiesterase genes and gene expression products such as mRNA. The polynucleotides can be used as hybridization probes to detect naturally-occurring genetic mutations in the phosphodiesterase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the phosphodiesterase gene associated with a dysfunction provides a diagnostic tool for an active disease or susceptibility to disease when the disease results from overexpression, underexpression, or altered expression of a phosphodiesterase.

Mutations in the phosphodiesterase gene can be detected at the nucleic acid level by a variety of techniques. Genomic DNA can be analyzed directly or can be amplified by using PCR prior to analysis. RNA or cDNA can be used in the same way.

In certain embodiments, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

Alternatively, mutations in a phosphodiesterase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site.

Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method.

Furthermore, sequence differences between a mutant phosphodiesterase gene and a wild-type gene can be determined by direct DNA sequencing. A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the gene include methods in which protection from cleavage agents is used to detect mismatched bases in RNA/RNA or RNA/DNA duplexes (Myers et al. (1985) *Science* 230:1242); Cotton et al. (1988) *PNAS* 85:4397; Saleeba et al. (1992) *Meth. Enzymol.* 217:286–295), electrophoretic mobility of mutant and wild type nucleic acid is compared (Orita et al. (1989) *PNAS* 86:2766; Cotton et al. (1993) *Mutat. Res.* 285:125–144; and Hayashi et al. (1992) *Genet. Anal. Tech. Appl.* 9:73–79), and movement of mutant or wild-type fragments in polyacrylamide gels containing a gradient of denaturant is assayed using denaturing gradient gel electrophoresis (Myers et al. (1985) *Nature* 313:495). The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet.* 7:5). Examples of other techniques for detecting point mutations include, selective oligonucleotide hybridization, selective amplification, and selective primer extension.

In other embodiments, genetic mutations can be identified by hybridizing a sample and control nucleic acids, e.g., DNA or RNA, to high density arrays containing hundreds or thousands of oligonucleotide probes (Cronin et al. (1996) *Human Mutation* 7:244–255; Kozal et al. (1996) *Nature Medicine* 2:753–759). For example, genetic mutations can be identified in two dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

The phosphodiesterase polynucleotides can also be used for testing an individual for a genotype that while not necessarily causing the disease, nevertheless affects the treatment modality. Thus, the polynucleotides can be used to study the relationship between an individual's genotype and the individual's response to a compound used for treatment (pharmacogenomic relationship). In the present case, for example, a mutation in the phosphodiesterase gene that results in altered affinity for cAMP or cGMP could result in an excessive or decreased drug effect with standard concentrations of cAMP or cGMP. Accordingly, the phosphodiesterase polynucleotides described herein can be used to assess the mutation content of the gene in an individual in order to select an appropriate compound or dosage regimen for treatment.

Thus polynucleotides displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The methods can involve obtaining a control biological sample from a control subject, contacting the control sample with a compound or agent capable of detecting mRNA, or genomic DNA, such that the presence of mRNA or genomic DNA is detected in the biological sample, and comparing the presence of mRNA or genomic DNA in the control sample with the presence of mRNA or genomic DNA in the test sample.

The phosphodiesterase polynucleotides can further be used to provide polynucleotide reagents, e.g., labeled or labelable probes which can be used in, for example, an in situ hybridization technique, to identify a specific tissue. This is useful in cases in which a forensic pathologist is presented with a tissue of unknown origin. Panels of phosphodiesterase probes can be used to identify tissue by species and/or by organ type.

In a similar fashion, these primers and probes can be used to screen tissue culture for contamination (i.e. screen for the presence of a mixture of different types of cells in a culture).

Alternatively, the phosphodiesterase polynucleotides can be used directly to block transcription or translation of phosphodiesterase gene sequences by means of antisense or ribozyme constructs. Thus, in a disorder characterized by abnormally high or undesirable phosphodiesterase gene expression, nucleic acids can be directly used for treatment.

The phosphodiesterase polynucleotides are thus useful as antisense constructs to control phosphodiesterase gene expression in cells, tissues, and organisms. A DNA antisense polynucleotide is designed to be complementary to a region of the gene involved in transcription, preventing transcription and hence production of phosphodiesterase protein. An antisense RNA or DNA polynucleotide would hybridize to the mRNA and thus block translation of mRNA into phosphodiesterase protein.

Examples of antisense molecules useful to inhibit nucleic acid expression include antisense molecules complementary to a fragment of the 5' untranslated region of SEQ ID NO 2 which also includes the start codon and antisense molecules which are complementary to a fragment of the 3' untranslated region of SEQ ID NO 2.

Alternatively, a class of antisense molecules can be used to inactivate mRNA in order to decrease expression of phosphodiesterase nucleic acid. Accordingly, these molecules can treat a disorder characterized by abnormal or undesired phosphodiesterase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the phosphodiesterase protein.

The phosphodiesterase polynucleotides also provide vectors for gene therapy in patients containing cells that are aberrant in phosphodiesterase gene expression. Thus, recombinant cells, which include the patient's cells that have been engineered ex vivo and returned to the patient, are introduced into an individual where the cells produce the desired phosphodiesterase protein to treat the individual.

The invention also encompasses kits for detecting the presence of a phosphodiesterase nucleic acid in a biological sample. For example, the kit can comprise reagents such as a labeled or labelable nucleic acid or agent capable of detecting phosphodiesterase nucleic acid in a biological sample; means for determining the amount of phosphodiesterase nucleic acid in the sample; and means for comparing the amount of phosphodiesterase nucleic acid in the sample with a standard. The compound or agent can be packaged in a suitable container. The kit can further comprise instructions for using the kit to detect phosphodiesterase mRNA or DNA.

Polynucleotides

The methods and uses described herein can be based on the phosphodiesterase polynucleotide as a reagent or as a target.

The invention thus provides methods and uses for the nucleotide sequence in SEQ ID NO 2.

The specifically disclosed cDNA comprises the coding region and 5' and 3' untranslated sequences in SEQ ID NO 2.

The invention provides isolated polynucleotides encoding the phosphodiesterase. The term "phosphodiesterase polynucleotide" or "phosphodiesterase nucleic acid" refers to the sequences shown in SEQ ID NO 2 or SEQ ID NO 4 or in the deposited cDNAs. The term "phosphodiesterase polynucleotide" or "phosphodiesterase nucleic acid" further includes variants and fragments of the phosphodiesterase polynucleotides.

An "isolated" phosphodiesterase nucleic acid is one that is separated from other nucleic acid present in the natural source of the phosphodiesterase nucleic acid. Preferably, an "isolated" nucleic acid is free of sequences which naturally flank the phosphodiesterase nucleic acid (i.e., sequences located at the 5' and 3' ends of the nucleic acid) in the genomic DNA of the organism from which the nucleic acid is derived. However, there can be some flanking nucleotide sequences, for example up to about 5 KB. The important point is that the phosphodiesterase nucleic acid is isolated from flanking sequences such that it can be subjected to the specific manipulations described herein, such as recombinant expression, preparation of probes and primers, and other uses specific to the phosphodiesterase nucleic acid sequences.

Moreover, an "isolated" nucleic acid molecule, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

In some instances, the isolated material will form part of a composition (or example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

The phosphodiesterase polynucleotides can encode the mature protein plus additional amino or carboxyterminal amino acids, or amino acids interior to the mature polypeptide (when the mature form has more than one polypeptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

The phosphodiesterase polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification.

Phosphodiesterase polynucleotides can be in the form of RNA, such as mRNA, or in the form DNA, including cDNA and genomic DNA obtained by cloning or produced by chemical synthetic techniques or by a combination thereof The nucleic acid, especially DNA, can be double-stranded or single-stranded. Single-stranded nucleic acid can be the coding strand (sense strand) or the non-coding strand (antisense strand).

In one embodiment, the phosphodiesterase nucleic acid comprises only the coding region.

The invention further provides variant phosphodiesterase polynucleotides, and fragments thereof, that differ from the nucleotide sequence shown in SEQ ID NO 2 due to degeneracy of the genetic code and thus encode the same protein as that encoded by the nucleotide sequence shown in SEQ ID NO 2.

The invention also provides phosphodiesterase nucleic acid molecules encoding the variant polypeptides described herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Typically, variants have a substantial identity with a nucleic acid molecule of SEQ ID NO 2 and the complements thereof Variation can occur in either or both the coding and non-coding regions. The variations can produce both conservative and non-conservative amino acid substitutions.

Orthologs, homologs, and allelic variants can be identified using methods well known in the art. These variants comprise a nucleotide sequence encoding a phosphodiesterase that is at least about 60–65%, 65–70%, typically at least about 70–75%, more typically at least about 80–85%, and most typically at least about 90–95% or more homologous to the nucleotide sequence shown in SEQ ID NO 2 or a fragment of this sequence. Such nucleic acid molecules can readily be identified as being able to hybridize under stringent conditions, to the nucleotide sequence shown in SEQ ID NO 2 or a fragment of the sequence. It is understood that stringent hybridization does not indicate substantial homology where it is due to general homology, such as poly A sequences, or sequences common to all or most proteins, or all cyclic nucleotide phosphodiesterases.

As used herein, the term "hybridizes under stringent conditions" is intended to describe conditions for hybridization and washing under which nucleotide sequences encoding a polypeptide at least about 60–65% homologous to each other typically remain hybridized to each other. The conditions can be such that sequences at least about 65%, at least about 70%, at least about 75%, at least about 80%, at least about 90%, at least about 95% or more identical to each other remain hybridized to one another. Such stringent conditions are known to those skilled in the art and can be found in Current Protocols in Molecular Biology, John Wiley & Sons, N.Y. (1989), 6.3.1–6.3.6, incorporated by reference. One example of stringent hybridization conditions are hybridization in 6×sodium chloride/sodium citrate (SSC) at about 45° C., followed by one or more washes in 0.2×SSC, 0.1% SDS at 50–65° C. In another non-limiting example, nucleic acid molecules are allowed to hybridize in 6×sodium chloride/sodium citrate (SSC) at about 45° C., followed by one or more low stringency washes in 0.2× SSC/0.1% SDS at room temperature, or by one or more moderate stringency washes in 0.2×SSC/0.1% SDS at 42° C., or washed in 0.2×SSC/0.1% SDS at 65° C. for high stringency. In one embodiment, an isolated nucleic acid molecule that hybridizes under stringent conditions to the sequence of SEQ ID NO 1 or SEQ ID NO 3 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

As understood by those of ordinary skill, the exact conditions can be determined empirically and depend on ionic strength, temperature and the concentration of destabilizing agents such as formamide or denaturing agents such as SDS. Other factors considered in determining the desired hybridization conditions include the length of the nucleic acid sequences, base composition, percent mismatch between the hybridizing sequences and the frequency of occurrence of subsets of the sequences within other non-identical sequences. Thus, equivalent conditions can be determined by varying one or more of these parameters while maintaining a similar degree of identity or similarity between the two nucleic acid molecules.

The present invention also provides isolated nucleic acids that contain a single or double stranded fragment or portion that hybridizes under stringent conditions to the nucleotide sequence of SEQ ID NO 2 or the complement of SEQ ID NO 2. In one embodiment, the nucleic acid consists of a portion of the nucleotide sequence of SEQ ID NO 2 and the complement of SEQ ID NO 2. The nucleic acid fragments of the invention are at least about 15, preferably at least about 18, 20, 23 or 25 nucleotides, and can be 30, 40, 50, 100, 200, 500 or more nucleotides in length. Longer fragments, for example, 30 or more nucleotides in length, which encode antigenic proteins or polypeptides described herein are useful.

Furthermore, the invention provides polynucleotides that comprise a fragment of the full-length phosphodiesterase polynucleotide. The fragment can be single or double-stranded and can comprise DNA or RNA. The fragment can be derived from either the coding or the non-coding sequence.

In another embodiment an isolated phosphodiesterase nucleic acid encodes the entire coding region. In another embodiment the isolated phosphodiesterase nucleic acid encodes a sequence corresponding to the mature protein that may be from about amino acid 6 to the last amino acid. Other fragments include nucleotide sequences encoding the amino acid fragments described herein.

Thus, phosphodiesterase nucleic acid fragments further include sequences corresponding to the domains described herein, subregions also described, and specific functional sites. Phosphodiesterase nucleic acid fragments also include combinations of the domains, segments, and other functional sites described above. A person of ordinary skill in the art would be aware of the many permutations that are possible.

Where the location of the domains or sites have been predicted by computer analysis, one of ordinary skill would appreciate that the amino acid residues constituting these domains can vary depending on the criteria used to define the domains.

However, it is understood that a phosphodiesterase fragment includes any nucleic acid sequence that does not include the entire gene.

The invention also provides phosphodiesterase nucleic acid fragments that encode epitope bearing regions of the phosphodiesterase proteins described herein.

Methods Using Vectors and Host Cells

The methods using vectors and host cells are particularly relevant where vectors are expressed in the cells, tissues, and disorders shown in FIGS. 5–7, and otherwise discussed herein, or where the host cells are those that naturally express the gene, as shown in these figures and which may be the native or a recombinant cell expressing the gene.

It is understood that "host cells" and "recombinant host cells" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The host cells expressing the polypeptides described herein, and particularly recombinant host cells, have a variety of uses. First, the cells are useful for producing phosphodiesterase proteins or polypeptides that can be further purified to produce desired amounts of phosphodiesterase protein or fragments. Thus, host cells containing expression vectors are useful for polypeptide production, as well as cells producing significant amounts of the polypeptide, for example, the high-expressors shown in FIG. 6, in other words, fetal heart cell and testes.

Host cells are also useful for conducting cell-based assays involving the phosphodiesterase or phosphodiesterase fragments. Thus, a recombinant host cell expressing a native phosphodiesterase is useful to assay for compounds that stimulate or inhibit phosphodiesterase function. This includes cAMP or cGMP binding, gene expression at the level of transcription or translation, protein kinase A interaction, and components of the signal transduction pathway.

Host cells are also useful for identifying phosphodiesterase mutants in which these functions are affected. If the mutants naturally occur and give rise to a pathology, host cells containing the mutations are useful to assay compounds that have a desired effect on the mutant phosphodiesterase (for example, stimulating or inhibiting function) which may not be indicated by their effect on the native phosphodiesterase.

Recombinant host cells are also useful for expressing the chimeric polypeptides described herein to assess compounds that activate or suppress activation by means of a heterologous domain, segment, site, and the like, as disclosed herein.

Further, mutant phosphodiesterases can be designed in which one or more of the various functions is engineered to be increased or decreased (e.g., cAMP binding or kinase A binding) and used to augment or replace phosphodiesterase proteins in an individual. Thus, host cells can provide a therapeutic benefit by replacing an aberrant phosphodiesterase or providing an aberrant phosphodiesterase that provides a therapeutic result. In one embodiment, the cells provide phosphodiesterases that are abnormally active.

In another embodiment, the cells provide a phosphodiesterase that is abnormally inactive. This phosphodiesterase can compete with endogenous phosphodiesterase in the individual.

In another embodiment, cells expressing phosphodiesterases that cannot be activated are introduced into an individual in order to compete with endogenous phosphodiesterase for cAMP. For example, in the case in which excessive cAMP is part of a treatment modality, it may be necessary to inactivate this molecule at a specific point in treatment. Providing cells that compete for the molecule, but which cannot be affected by phosphodiesterase activation would be beneficial.

Homologously recombinant host cells can also be produced that allow the in situ alteration of endogenous phosphodiesterase polynucleotide sequences in a host cell genome. The host cell includes, but is not limited to, a stable cell line, cell in vivo, or cloned microorganism. This technology is more fully described in WO 93/09222, WO 91/12650, WO 91/06667, U.S. Pat. No. 5,272,071, and U.S. Pat. No. 5,641,670. Briefly, specific polynucleotide sequences corresponding to the phosphodiesterase polynucleotides or sequences proximal or distal to a phosphodiesterase gene are allowed to integrate into a host cell genome by homologous recombination where expression of the gene can be affected. In one embodiment, regulatory sequences are introduced that either increase or decrease expression of an endogenous sequence. Accordingly, a phosphodiesterase protein can be produced in a cell not normally producing it. Alternatively, increased expression of phosphodiesterase protein can be effected in a cell normally producing the protein at a specific level. Further, expression can be decreased or eliminated by introducing a specific regulatory sequence. The regulatory sequence can be heterologous to the phosphodiesterase protein sequence or can be a homologous sequence with a desired mutation that affects expression. Alternatively, the entire gene can be deleted. The regulatory sequence can be specific to the host cell or capable of functioning in more than one cell type. Still further, specific mutations can be introduced into any desired region of the gene to produce mutant phosphodiesterase proteins. Such mutations could be introduced, for example, into the specific functional regions such as the cyclic nucleotide-binding site.

In one embodiment, the host cell can be a fertilized oocyte or embryonic stem cell that can be used to produce a transgenic animal containing the altered phosphodiesterase gene. Alternatively, the host cell can be a stem cell or other early tissue precursor that gives rise to a specific subset of cells and can be used to produce transgenic tissues in an animal. See also Thomas et al, *Cell* 51:503 (1987) for a description of homologous recombination vectors. The vector is introduced into an embryonic stem cell line (e.g., by electroporation) and cells in which the introduced gene has homologously recombined with the endogenous phosphodiesterase gene is selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos. WO 90/11354; WO 91/01140; and WO 93/04169.

The genetically engineered host cells can be used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a phosphodiesterase protein and identifying and evaluating modulators of phosphodiesterase protein activity.

Other examples of transgenic animals include non-human primates, sheep, dogs, cows, goats, chickens, and amphibians.

In one embodiment, a host cell is a fertilized oocyte or an embryonic stem cell into which phosphodiesterase polynucleotide sequences have been introduced.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the phosphodiesterase nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the phosphodiesterase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems, which allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *S. cerevisiae* (O'Gorman et al. (1991) *Science* 251:1351–1355. If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female foster animal will be a clone of the animal from which the cell, e.g., the somatic cell, is isolated.

Transgenic animals containing recombinant cells that express the polypeptides described herein are useful to conduct the assays described herein in an in vivo context. Accordingly, the various physiological factors that are present in vivo and that could affect cAMP binding, phosphodiesterase activation, and signal transduction, may not be evident from in vitro cell-free or cell-based assays. Accordingly, it is useful to provide non-human transgenic animals to assay in vivo phosphodiesterase function, including cAMP interaction, the effect of specific mutant phosphodiesterases on phosphodiesterase function and cAMP interaction, and the effect of chimeric phosphodiesterases. It is also possible to assess the effect of null mutations, that is mutations that substantially or completely eliminate one or more phosphodiesterase functions.

In general, methods for producing transgenic animals include introducing a nucleic acid sequence according to the present invention, the nucleic acid sequence capable of expressing the protein in a transgenic animal, into a cell in culture or in vivo. When introduced in vivo, the nucleic acid is introduced into an intact organism such that one or more cell types and, accordingly, one or more tissue types, express the nucleic acid encoding the protein. Alternatively, the nucleic acid can be introduced into virtually all cells in an organism by transfecting a cell in culture, such as an embryonic stem cell, as described herein for the production of transgenic animals, and this cell can be used to produce an entire transgenic organism. As described, in a further embodiment, the host cell can be a fertilized oocyte. Such cells are then allowed to develop in a female foster animal to produce the transgenic organism.

Vectors/Host Cells

The methods using the vectors and host cells discussed above are based on the vectors and host cells including, but not limited to, those described below.

The invention also provides methods using vectors containing the phosphodiesterase polynucleotides. The term "vector" refers to a vehicle, preferably a nucleic acid molecule that can transport the phosphodiesterase polynucleotides. When the vector is a nucleic acid molecule, the phosphodiesterase polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the phosphodiesterase polynucleotides. Alternatively, the vector may integrate into the host cell genome and produce additional copies of the phosphodiesterase polynucleotides when the host cell replicates.

The invention provides vectors for the maintenance (cloning vectors) or vectors for expression (expression vectors) of the phosphodiesterase polynucleotides. The vectors can function in procaryotic or eukaryotic cells or in both (shuttle vectors).

Expression vectors contain cis-acting regulatory regions that are operably linked in the vector to the phosphodiesterase polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of the phosphodiesterase polynucleotides from the vector. Alternatively, a trans-acting factor may be supplied by the host cell. Finally, a trans-acting factor can be produced from the vector itself.

It is understood, however, that in some embodiments, transcription and/or translation of the phosphodiesterase polynucleotides can occur in a cell-free system.

The regulatory sequence to which the polynucleotides described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al. (1989) *Molecular Cloning: A Laboratory Manual 2nd. ed.*, Cold Spring Harbor Laboratory Press, Cold Spring Harbor, N.Y.).

A variety of expression vectors can be used to express a phosphodiesterase polynucleotide. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al. (1989) *Molecular Cloning: A Laboratory Manual 2nd ed.*, Cold Spring Harbor Laboratory Press, Cold Spring Harbor, N.Y.

The regulatory sequence may provide constitutive expression in one or more host cells (i.e., tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The phosphodiesterase polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the polypeptide as a fusion protein. Accordingly, the invention provides fusion vectors that allow for the production of the phosphodiesterase polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, thrombin, and enterokinase. Typical fusion expression vectors include pGEX (Smith et al. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion E. coli expression vectors include pTrc (Amann et al. (1988) Gene 69:301–315) and pET 11d (Studier et al. (1990) Gene Expression Technology: Methods in Enzymology 185:60–89).

Recombinant protein expression can be maximized in a host bacteria by providing a genetic background wherein the host cell has an impaired capacity to proteolytically cleave the recombinant protein. (Gottesman, S. (1990) Gene Expression Technology: Methods in Enzymology 185, Academic Press, San Diego, Calif. 119–128). Alternatively, the sequence of the polynucleotide of interest can be altered to provide preferential codon usage for a specific host cell, for example E. coli. (Wada et al. (1992) Nucleic Acids Res. 20:2111–2118).

The phosphodiesterase polynucleotides can also be expressed by expression vectors that are operative in yeast. Examples of vectors for expression in yeast e.g., S. cerevisiae include pYepSec1 (Baldari et al. (1987) EMBO J. 6:229–234), pMFa (Kurjan et al. (1982) Cell 30:933–943), pJRY88 (Schultz et al. (1987) Gene 54:113–123), and pYES2 (Invitrogen Corporation, San Diego, Calif.).

The phosphodiesterase polynucleotides can also be expressed in insect cells using, for example, baculovirus expression vectors. Baculovirus vectors available for expression of proteins in cultured insect cells (e.g., Sf 9 cells) include the pAc series (Smith et al. (1983) Mol. Cell Biol. 3:2156–2165) and the pVL series (Lucklow et al. (1989) Virology 170:31–39).

In certain embodiments of the invention, the polynucleotides described herein are expressed in mammalian cells using mammalian expression vectors. Examples of mammalian expression vectors include pCDM8 (Seed, B. (1987) Nature 329:840) and pMT2PC (Kaufman et al. (1987) EMBO J. 6:187–195).

The expression vectors listed herein are provided by way of example only of the well-known vectors available to those of ordinary skill in the art that would be useful to express the phosphodiesterase polynucleotides. The person of ordinary skill in the art would be aware of other vectors suitable for maintenance propagation or expression of the polynucleotides described herein. These are found for example in Sambrook et al. (1989) Molecular Cloning: A Laboratory Manual 2nd, ed., Cold Spring Harbor Laboratory, Cold Spring Harbor Laboratory Press, Cold Spring Harbor, N.Y.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook et al. (Molecular Cloning: A Laboratory Manual, 2d ed., Cold Spring Harbor Laboratory, Cold Spring Harbor Laboratory Press, Cold Spring Harbor, N.Y.).

Host cells can contain more than one vector. Thus, different nucleotide sequences can be introduced on different vectors of the same cell. Similarly, the phosphodiesterase polynucleotides can be introduced either alone or with other polynucleotides that are not related to the phosphodiesterase polynucleotides such as those providing trans-acting factors for expression vectors. When more than one vector is introduced into a cell, the vectors can be introduced independently, co-introduced or joined to the phosphodiesterase polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the phosphodiesterase polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

Pharmaceutical Compositions

The invention encompasses use of the polypeptides, nucleic acids, and other agents in pharmaceutical compositions to administer to the cells in which expression of the phosophodiesterase is relevant and in disorders as disclosed herein. Uses are both diagnostic and therapeutic. The phosphodiesterase nucleic acid molecules, protein, modulators of the protein, and antibodies (also referred to herein as "active compounds") can be incorporated into pharmaceutical compositions suitable for administration to a subject, e.g., a human. Such compositions typically comprise the nucleic acid molecule, protein, modulator, or antibody and a pharmaceutically acceptable carrier. It is understood however, that administration can also be to cells in vitro as well as to in vivo model systems such as non-human transgenic animals.

The term "administer" is used in its broadest sense and includes any method of introducing the compositions of the present invention into a subject. This includes producing polypeptides or polynucleotides in vivo as by transcription or translation, in vivo, of polynucleotides that have been exogenously introduced into a subject. Thus, polypeptides or nucleic acids produced in the subject from the exogenous compositions are encompassed in the term "administer."

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a phosphodiesterase protein or anti-phosphodiesterase antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see e.g., Chen et al. (1994) PNAS 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

That which is claimed:

1. A method of identifying an agent that binds a human cyclic phosphodiesterase protein comprising:
   a) combining an agent to be tested with a host cell expressing human cyclic phosphodiesterase protein having an amino acid sequence as set forth in SEQ ID NO:1 under conditions suitable for binding of said agent to said human cyclic phosphodiesterase protein; and
   b) detecting the formation of a complex between said agent and said human cyclic phosphodiesterase protein;
   wherein said host cell is selected from the group consisting of breast carcinoma cells and colon carcinoma cells.

2. The method of claim 1, wherein said method is a competition assay, in which binding is determined in the presence of one or more agents.

3. The method of claim 1, wherein said human cyclic phosphodiesterase protein can mediate cellular signaling or a cellular response, and the formation of a complex is monitored by detecting a signaling activity or cellular response of said cyclic phosphodiesterase protein in response thereto.

4. A method of identifying an agent that binds a human cyclic phosphodiesterase protein comprising:
   a) combining an agent to be tested with a host cell expressing a fusion protein comprising SEQ ID NO:1 under conditions suitable for binding of said agent to said fusion protein; and
   b) detecting the formation of a complex between said agent and said fusion protein;
   wherein said host cell is selected from the group consisting of breast carcinoma cells and colon carcinoma cells.

5. The method of claim 4, wherein said method is a competition assay, in which binding is determined in the presence of one or more agents.

6. The method of claim 4, wherein said fusion protein can mediate cellular signaling or a cellular response, and the formation of a complex is monitored by detecting a signaling activity or cellular response of said fusion protein in response thereto.

7. The method of claim 1, wherein said human cyclic phosphodiesterase protein having the amino acid sequence set forth in SEQ ID NO:1 is encoded by the nucleotide sequence set forth in SEQ ID NO:2.

8. The method of claim 7 wherein said method is a competition assay, in which binding is determined in the presence of one or more agents.

9. The method of claim 7, wherein said human cyclic phosphodiesterase protein can mediate cellular signaling or a cellular response, and the formation of a complex is monitored by detecting a signaling activity or cellular response of said cyclic phosphodiesterase protein in response thereto.

10. The method of claim 4, wherein the amino acid sequence set forth in SEQ ID NO:1 is encoded by the nucleotide sequence set forth in SEQ ID NO:2.

11. The method of claim 10, wherein said method is a competition assay, in which binding is determined in the presence of one or more agents.

12. The method of claim 10, wherein said fusion protein can mediate cellular signaling or a cellular response, and the formation of a complex is monitored by detecting a signaling activity or cellular response of said fusion protein in response thereto.

* * * * *

SEQUENCE LISTING

<160> NUMBER OF SEQ ID NOS: 2

<210> SEQ ID NO 1
<211> LENGTH: 779
<212> TYPE: PRT
<213> ORGANISM: Homo sapiens

<400> SEQUENCE: 1

```
Met Arg Ile Glu Glu Arg Lys Ser Gln His Leu Thr Gly Leu Thr Asp
  1               5                  10                  15

Glu Lys Val Lys Ala Tyr Leu Ser Leu His Pro Gln Val Leu Asp Glu
             20                  25                  30

Phe Val Ser Glu Ser Val Ser Ala Glu Thr Val Glu Lys Trp Leu Lys
         35                  40                  45

Arg Lys Asn Asn Lys Ser Glu Asp Glu Ser Ala Pro Lys Glu Val Ser
 50                  55                  60

Arg Tyr Gln Asp Thr Asn Met Gln Gly Val Val Tyr Glu Leu Asn Ser
 65                  70                  75                  80

Tyr Ile Glu Gln Arg Leu Asp Thr Gly Asp Asn Gln Leu Leu Leu
                 85                  90                  95

Tyr Glu Leu Ser Ser Ile Ile Lys Ile Ala Thr Lys Ala Asp Gly Phe
            100                 105                 110

Ala Leu Tyr Phe Leu Gly Glu Cys Asn Asn Ser Leu Cys Ile Phe Thr
        115                 120                 125

Pro Pro Gly Ile Lys Glu Gly Lys Pro Arg Leu Ile Pro Ala Gly Pro
130                 135                 140

Ile Thr Gln Gly Thr Thr Val Ser Ala Tyr Val Ala Lys Ser Arg Lys
145                 150                 155                 160

Thr Leu Leu Val Glu Asp Ile Leu Gly Asp Glu Arg Phe Pro Arg Gly
                165                 170                 175

Thr Gly Leu Glu Ser Gly Thr Arg Ile Gln Ser Val Leu Cys Leu Pro
            180                 185                 190

Ile Val Thr Ala Ile Gly Asp Leu Ile Gly Ile Leu Glu Leu Tyr Arg
        195                 200                 205

His Trp Gly Lys Glu Ala Phe Cys Leu Ser His Gln Glu Val Ala Thr
    210                 215                 220

Ala Asn Leu Ala Trp Ala Ser Val Ala Ile His Gln Val Gln Val Cys
225                 230                 235                 240

Arg Gly Leu Ala Lys Gln Thr Glu Leu Asn Asp Phe Leu Leu Asp Val
                245                 250                 255

Ser Lys Thr Tyr Phe Asp Asn Ile Val Ala Ile Asp Ser Leu Leu Glu
            260                 265                 270

His Ile Met Ile Tyr Ala Lys Asn Leu Val Asn Ala Asp Arg Cys Ala
        275                 280                 285

Leu Phe Gln Val Asp His Lys Asn Lys Glu Leu Tyr Ser Asp Leu Phe
    290                 295                 300

Asp Ile Gly Glu Glu Lys Glu Gly Lys Pro Val Phe Lys Lys Thr Lys
305                 310                 315                 320

Glu Ile Arg Phe Ser Ile Glu Lys Gly Ile Ala Gly Gln Val Ala Arg
                325                 330                 335

Thr Gly Glu Val Leu Asn Ile Pro Asp Ala Tyr Ala Asp Pro Arg Phe
            340                 345                 350

Asn Arg Glu Val Asp Leu Tyr Thr Gly Tyr Thr Thr Arg Asn Ile Leu
```

-continued

```
            355                 360                 365
Cys Met Pro Ile Val Ser Arg Gly Ser Val Ile Gly Val Val Gln Met
        370                 375                 380
Val Asn Lys Ile Ser Gly Ser Ala Phe Ser Lys Thr Asp Glu Asn Asn
385                 390                 395                 400
Phe Lys Met Phe Ala Val Phe Cys Ala Leu Ala Leu His Cys Ala Asn
                405                 410                 415
Met Tyr His Arg Ile Arg His Ser Glu Cys Ile Tyr Arg Val Thr Met
            420                 425                 430
Glu Lys Leu Ser Tyr His Ser Ile Cys Thr Ser Glu Glu Trp Gln Gly
            435                 440                 445
Leu Met Gln Phe Thr Leu Pro Val Arg Leu Cys Lys Glu Ile Glu Leu
        450                 455                 460
Phe His Phe Asp Ile Gly Pro Phe Glu Asn Met Trp Pro Gly Ile Phe
465                 470                 475                 480
Val Tyr Met Val His Arg Ser Cys Gly Thr Ser Cys Phe Glu Leu Glu
                485                 490                 495
Lys Leu Cys Arg Phe Ile Met Ser Val Lys Lys Asn Tyr Arg Arg Val
                500                 505                 510
Pro Tyr His Asn Trp Lys His Ala Val Thr Val Ala His Cys Met Tyr
            515                 520                 525
Ala Ile Leu Gln Asn Asn His Thr Leu Phe Thr Asp Leu Glu Arg Lys
        530                 535                 540
Gly Leu Leu Ile Ala Cys Leu Cys His Asp Leu Asp His Arg Gly Phe
545                 550                 555                 560
Ser Asn Ser Tyr Leu Gln Lys Phe Asp His Pro Leu Ala Ala Leu Tyr
                565                 570                 575
Ser Thr Ser Thr Met Glu Gln His His Phe Ser Gln Thr Val Ser Ile
            580                 585                 590
Leu Gln Leu Glu Gly His Asn Ile Phe Ser Thr Leu Ser Ser Ser Glu
        595                 600                 605
Tyr Glu Gln Val Leu Glu Ile Ile Arg Lys Ala Ile Ile Ala Thr Asp
610                 615                 620
Leu Ala Leu Tyr Phe Gly Asn Arg Lys Gln Leu Glu Glu Met Tyr Gln
625                 630                 635                 640
Thr Gly Ser Leu Asn Leu Asn Asn Gln Ser His Arg Asp Arg Val Ile
                645                 650                 655
Gly Leu Met Met Thr Ala Cys Asp Leu Cys Ser Val Thr Lys Leu Trp
                660                 665                 670
Pro Val Thr Lys Leu Thr Ala Asn Asp Ile Tyr Ala Glu Phe Trp Ala
            675                 680                 685
Glu Gly Asp Glu Met Lys Lys Leu Gly Ile Gln Pro Ile Pro Met Met
        690                 695                 700
Asp Arg Asp Lys Lys Asp Glu Val Pro Gln Gly Gln Leu Gly Phe Tyr
705                 710                 715                 720
Asn Ala Val Ala Ile Pro Cys Tyr Thr Thr Leu Thr Gln Ile Leu Pro
                725                 730                 735
Pro Thr Glu Pro Leu Leu Lys Ala Cys Arg Asp Asn Leu Ser Gln Trp
            740                 745                 750
Glu Lys Val Ile Arg Gly Glu Glu Thr Ala Thr Trp Ile Ser Ser Pro
        755                 760                 765
Ser Val Ala Gln Lys Ala Ala Ala Ser Glu Asp
        770                 775
```

```
<210> SEQ ID NO 2
<211> LENGTH: 4381
<212> TYPE: DNA
<213> ORGANISM: Homo sapiens
<220> FEATURE:
<221> NAME/KEY: CDS
<222> LOCATION: (67)...(2403)

<400> SEQUENCE: 2
catccacaga gatgttacag ttgaagagat gggggtagag aagactttga aggaaaagaa      60
tgtaga atg agg ata gaa gag agg aaa tcc caa cat tta aca ggt ttg        108
       Met Arg Ile Glu Glu Arg Lys Ser Gln His Leu Thr Gly Leu
         1               5                  10 aca gat gaa aaa gtg aag gca tat ctt tct ctt cac ccc cag gta tta       156
Thr Asp Glu Lys Val Lys Ala Tyr Leu Ser Leu His Pro Gln Val Leu
 15                  20                  25                  30 gat gaa ttt gta tct gaa agt gtt agt gca gag aca gta gag aaa tgg       204
Asp Glu Phe Val Ser Glu Ser Val Ser Ala Glu Thr Val Glu Lys Trp
                 35                  40                  45 ctg aag agg aag aac aac aaa tca gaa gat gaa tcg gct cct aag gaa       252
Leu Lys Arg Lys Asn Asn Lys Ser Glu Asp Glu Ser Ala Pro Lys Glu
             50                  55                  60 gtc agc agg tac caa gat acg aat atg cag gga gtt gta tat gaa cta       300
Val Ser Arg Tyr Gln Asp Thr Asn Met Gln Gly Val Val Tyr Glu Leu
         65                  70                  75 aac agc tat ata gaa caa cgg ttg gac aca gga gga gac aac cag cta       348
Asn Ser Tyr Ile Glu Gln Arg Leu Asp Thr Gly Gly Asp Asn Gln Leu
     80                  85                  90 ctc ctc tat gaa ctg agc agc atc att aaa ata gcc aca aaa gcc gat       396
Leu Leu Tyr Glu Leu Ser Ser Ile Ile Lys Ile Ala Thr Lys Ala Asp
 95                 100                 105                 110 gga ttt gca ctg tat ttc ctt gga gag tgc aat aat agc ctg tgt ata       444
Gly Phe Ala Leu Tyr Phe Leu Gly Glu Cys Asn Asn Ser Leu Cys Ile
                115                 120                 125 ttc acg cca cct ggg ata aag gaa gga aaa ccc cgc ctc atc cct gct       492
Phe Thr Pro Pro Gly Ile Lys Glu Gly Lys Pro Arg Leu Ile Pro Ala
            130                 135                 140 ggg ccc atc act cag ggc acc acc gtc tct gct tat gtg gcc aag tcc       540
Gly Pro Ile Thr Gln Gly Thr Thr Val Ser Ala Tyr Val Ala Lys Ser
        145                 150                 155 agg aaa aca ctg cta gta gaa gac atc ctt gga gat gaa cga ttt cca       588
Arg Lys Thr Leu Leu Val Glu Asp Ile Leu Gly Asp Glu Arg Phe Pro
    160                 165                 170 aga ggt act gga ctg gaa tca ggg act cgt atc cag tct gtt ctt tgc       636
Arg Gly Thr Gly Leu Glu Ser Gly Thr Arg Ile Gln Ser Val Leu Cys
175                 180                 185                 190 tta cca att gtc act gca att ggt gac ttg att ggt att ctc gag ctg       684
Leu Pro Ile Val Thr Ala Ile Gly Asp Leu Ile Gly Ile Leu Glu Leu
                195                 200                 205 tat cgg cac tgg ggc aaa gaa gcc ttc tgt ctt agt cac cag gag gtt       732
Tyr Arg His Trp Gly Lys Glu Ala Phe Cys Leu Ser His Gln Glu Val
            210                 215                 220 gca aca gca aat ctt gcc tgg gct tca gta gca ata cat cag gtg cag       780
Ala Thr Ala Asn Leu Ala Trp Ala Ser Val Ala Ile His Gln Val Gln
        225                 230                 235 gta tgc aga ggc ctt gcc aaa cag aca gaa ttg aat gac ttc cta ctc       828
Val Cys Arg Gly Leu Ala Lys Gln Thr Glu Leu Asn Asp Phe Leu Leu
    240                 245                 250 gac gta tca aaa aca tat ttt gat aac ata gtt gca ata gat tct cta       876
Asp Val Ser Lys Thr Tyr Phe Asp Asn Ile Val Ala Ile Asp Ser Leu
```

```
                        255                 260                 265                 270
cct gaa cac ata atg ata tat gca aaa aac ctg gtg aat gcc gat cgt                      924
Leu Glu His Ile Met Ile Tyr Ala Lys Asn Leu Val Asn Ala Asp Arg
                275                 280                 285 tgt gca ctt ttc cag gtg gac cat aag aac aag gag tta tat tca gac                      972
Cys Ala Leu Phe Gln Val Asp His Lys Asn Lys Glu Leu Tyr Ser Asp
                290                 295                 300 ctt ttt gat att gga gag gaa aag gaa gga aaa cct gtc ttc aag aag                     1020
Leu Phe Asp Ile Gly Glu Glu Lys Glu Gly Lys Pro Val Phe Lys Lys
                305                 310                 315 acc aaa gag ata aga ttt tca att gag aaa gga att gct ggc caa gta                     1068
Thr Lys Glu Ile Arg Phe Ser Ile Glu Lys Gly Ile Ala Gly Gln Val
                320                 325                 330 gca aga aca ggg gaa gtc ctg aac att cca gat gcc tat gca gac cca                     1116
Ala Arg Thr Gly Glu Val Leu Asn Ile Pro Asp Ala Tyr Ala Asp Pro
335                 340                 345                 350 cgc ttt aac aga gaa gta gac ttg tac aca ggc tac acc acg cgg aac                     1164
Arg Phe Asn Arg Glu Val Asp Leu Tyr Thr Gly Tyr Thr Thr Arg Asn
                355                 360                 365 atc ctg tgc atg ccc atc gtc agc cga ggc agc gtg ata ggt gtg gtg                     1212
Ile Leu Cys Met Pro Ile Val Ser Arg Gly Ser Val Ile Gly Val Val
                370                 375                 380 cag atg gtc aac aaa atc agt ggc agt gcc ttc tct aaa aca gat gaa                     1260
Gln Met Val Asn Lys Ile Ser Gly Ser Ala Phe Ser Lys Thr Asp Glu
                385                 390                 395 aac aac ttc aaa atg ttt gcc gtc ttt tgt gct tta gcc tta cac tgt                     1308
Asn Asn Phe Lys Met Phe Ala Val Phe Cys Ala Leu Ala Leu His Cys
                400                 405                 410 gct aat atg tat cat aga att cgc cac tca gag tgc att tac cgg gta                     1356
Ala Asn Met Tyr His Arg Ile Arg His Ser Glu Cys Ile Tyr Arg Val
415                 420                 425                 430 acg atg gaa aag ctg tcc tac cat agc att tgt act tca gaa gag tgg                     1404
Thr Met Glu Lys Leu Ser Tyr His Ser Ile Cys Thr Ser Glu Glu Trp
                435                 440                 445 caa ggt ctc atg caa ttc acc ctt ccc gtg cgt ctc tgc aaa gaa att                     1452
Gln Gly Leu Met Gln Phe Thr Leu Pro Val Arg Leu Cys Lys Glu Ile
                450                 455                 460 gaa tta ttc cac ttt gac att ggt cct ttt gaa aac atg tgg cct gga                     1500
Glu Leu Phe His Phe Asp Ile Gly Pro Phe Glu Asn Met Trp Pro Gly
                465                 470                 475 att ttt gtc tac atg gtt cat cgg tcc tgt ggg aca tcc tgc ttt gag                     1548
Ile Phe Val Tyr Met Val His Arg Ser Cys Gly Thr Ser Cys Phe Glu
                480                 485                 490 ctt gaa aag ttg tgt cgt ttt att atg tct gtg aag aag aac tat cgg                     1596
Leu Glu Lys Leu Cys Arg Phe Ile Met Ser Val Lys Lys Asn Tyr Arg
495                 500                 505                 510 cgg gtt cct tat cac aac tgg aag cat gcg gtc act gta gca cac tgc                     1644
Arg Val Pro Tyr His Asn Trp Lys His Ala Val Thr Val Ala His Cys
                515                 520                 525 atg tat gcc ata ctt cag aac aat cac acg ctt ttc aca gac ctt gag                     1692
Met Tyr Ala Ile Leu Gln Asn Asn His Thr Leu Phe Thr Asp Leu Glu
                530                 535                 540 cgc aaa gga ctg ctg att gcg tgt ctg tgt cat gac ctg gac cac agg                     1740
Arg Lys Gly Leu Leu Ile Ala Cys Leu Cys His Asp Leu Asp His Arg
                545                 550                 555 ggc ttc agt aac agc tac ctg cag aag ttc gac cac cct ctg gcc gct                     1788
Gly Phe Ser Asn Ser Tyr Leu Gln Lys Phe Asp His Pro Leu Ala Ala
                560                 565                 570 ctc tac tcc act tcc acc atg gag cag cac cac ttc tcc cag act gtg                     1836
```

```
                                                          -continued

Leu Tyr Ser Thr Ser Thr Met Glu Gln His His Phe Ser Gln Thr Val
575                 580                 585                 590 tcc atc ctc cag ttg gaa ggg cac aat atc ttc tcc act ctg agc tcc      1884
Ser Ile Leu Gln Leu Glu Gly His Asn Ile Phe Ser Thr Leu Ser Ser
            595                 600                 605 agt gaa tat gag cag gtg ctt gag atc atc cgc aaa gcc atc att gcc      1932
Ser Glu Tyr Glu Gln Val Leu Glu Ile Ile Arg Lys Ala Ile Ile Ala
        610                 615                 620 aca gac ctt gct tta tac ttt gga aac agg aag cag ttg gaa gag atg      1980
Thr Asp Leu Ala Leu Tyr Phe Gly Asn Arg Lys Gln Leu Glu Glu Met
    625                 630                 635 tac cag acc gga tca cta aac ctt aat aat caa tca cat aga gac cgt      2028
Tyr Gln Thr Gly Ser Leu Asn Leu Asn Asn Gln Ser His Arg Asp Arg
640                 645                 650 gta att ggt ttg atg atg act gcc tgt gac ctt tgt tct gtg aca aaa      2076
Val Ile Gly Leu Met Met Thr Ala Cys Asp Leu Cys Ser Val Thr Lys
655                 660                 665                 670 ctg tgg ccc gtt aca aaa ttg acg gca aat gat ata tat gca gaa ttc      2124
Leu Trp Pro Val Thr Lys Leu Thr Ala Asn Asp Ile Tyr Ala Glu Phe
            675                 680                 685 tgg gct gag ggt gat gaa atg aag aaa ttg gga ata cag cct att cct      2172
Trp Ala Glu Gly Asp Glu Met Lys Lys Leu Gly Ile Gln Pro Ile Pro
        690                 695                 700 atg atg gac aga gac aag aag gat gaa gtc ccc caa ggc cag ctt ggg      2220
Met Met Asp Arg Asp Lys Lys Asp Glu Val Pro Gln Gly Gln Leu Gly
    705                 710                 715 ttc tac aat gcc gtg gcc att ccc tgc tat aca acc ctt acc cag atc      2268
Phe Tyr Asn Ala Val Ala Ile Pro Cys Tyr Thr Thr Leu Thr Gln Ile
720                 725                 730 ctc cct ccc acg gag cct ctt ctg aaa gca tgc agg gat aat ctc agt      2316
Leu Pro Pro Thr Glu Pro Leu Leu Lys Ala Cys Arg Asp Asn Leu Ser
735                 740                 745                 750 cag tgg gag aag gtg att cga ggg gag gag act gca acc tgg att tca      2364
Gln Trp Glu Lys Val Ile Arg Gly Glu Glu Thr Ala Thr Trp Ile Ser
            755                 760                 765 tcc cca tcc gtg gct cag aag gca gct gca tct gaa gat tgagcactgg       2413
Ser Pro Ser Val Ala Gln Lys Ala Ala Ala Ser Glu Asp
        770                 775 tcaccctgac acgctgtccc acctacagat cctcatcttg cttctttgac attctttcc    2473 tttttttggg gggggtgggg ggaacctgca cctggtaact ggggtgcaaa cctcttcaag    2533
aaggtaacat caaataaata agtcaagcag aggacttcct gccaatctct tctgtgaggc    2593
atcatagaca ctgagcaacc aggaccaccc ccacgttcag aaatcagctg gccaagtgac    2653
tccatttgac ttgcaaacca gccttttcta ataggctaat attgctgagg ccttaaagga    2713
aatggacaaa aattatccag aagggtact  tttccattgt atctttctaa taagggttta    2773
aaatggtact attatggtat tgtacttggg ctttaacatc aatgttgctt tgatgttgtt    2833
ggatataaat aggaattttt acacattact attgtgaatg gtgaatgttc atgtatgacc    2893
tacttgtaat taacttgagt tgtagtccac agcctcagga caaatgtcgt tgaggttaca    2953
gagtaagaaa tgatggcaaa acgtcaaact cttatttcag agcttcatga atttagttag    3013
actaaacata attcttttaag ttcaacctaa agggctgaga tcaataaatt taacactaga   3073
cgaagtagac ttcctgtctt tttgagaaga gatgaggtat atgttacaat aaatctcaga    3133
acttcaagta gcagttcaaa agatgtcagt ttttaaaatt gttttttgttg ttgtcttggc   3193 agttttactg aaccctttgc ataaagaaca aaataaaagc tcggcattgt aattttttta   3253
```

-continued

```
atggacaagt cttatggata cgaagggtac atttttcata atgattcctt tatattttca    3313
ctttgtgtca ttgcagaatt ttagactctc attcacaatg aaaagtttat tttaaacatt    3373
gtttaattaa aataccatac agttctcttt taaacatcaa accataaaaa gtgtattttg    3433
taattttact ctgacctgcc gcagtcacct ctcacttatc tcttccacgt actgcacggt    3493
cgtatttcat gagctttctg tccatagcac agaaacagag cagaaagtag tacaatcatg    3553
ttggaccttc tttctgttct ctttactctt ctcacagatc agatcactcc atagaagcct    3613
gtgggtttcg atggtttctt ctatacacct ttttggttga ccagtattac tatacaatgt    3673
aagtgtttta aaaaatacga aagtaatact ctgcacccct tcctacaaag atgataaagc    3733
agtcacttct ggcgcatttt aataatttaa agattttag tgcaatggca cggtaacctc     3793
caaacctgaa ttagacagag actcactcag gaagtgacag gcccatcata tcaaataact    3853
tattcacttt tcatgtggca ggaaactgga atatcgcttt taataaaatg gaaaaatatg    3913
cttctacata tttaccacca taggcgtttt gttcatatga gcctggtttg tgcaaaatta    3973
aatcagaggc ttctacaaca tggtttattt atgttgtagc aaagttggct ctacataaac    4033
attgttctta tttaaaatt aacactatgt gttcagtttt cttgtgggct tctgaaagtt     4093
gccatcttcc ctccgtggag ctccatttgc tattttcatt atacactatg aggtaaaatg    4153
taataacaaa agagagagaa gtaccactgt ggctagatat atacacacac atatatatat    4213
ggatggatgt aatatatgta gaacacacac atagatgtat ataggataca cactcatgta    4273
tgtaaacgta tacatatgtg tatatatgat acatacacat acacacacac gagagacaga    4333
aggaaagaga ggaagagaga agcaaacatg taggaaaaaa tataaatc                 4381
```